US007559530B2

(12) United States Patent
Korogi et al.

(10) Patent No.: US 7,559,530 B2
(45) Date of Patent: Jul. 14, 2009

(54) VALVED FLUID CONNECTOR

(75) Inventors: Todd M. Korogi, Raleigh, NC (US); Scott P. Jarnagin, Seattle, WA (US); Theodore J. Mosler, Raleigh, NC (US)

(73) Assignee: Industrie Borla S.p.A., Turin (IT)

( * ) Notice: Subject to any disclaimer, the term of this patent is extended or adjusted under 35 U.S.C. 154(b) by 427 days.

(21) Appl. No.: 11/353,275

(22) Filed: Feb. 13, 2006

(65) Prior Publication Data

US 2006/0192164 A1  Aug. 31, 2006

Related U.S. Application Data

(60) Provisional application No. 60/652,793, filed on Feb. 14, 2005.

(51) Int. Cl.
  F16K 51/00   (2006.01)
  F16L 29/00   (2006.01)
  F16L 37/28   (2006.01)
(52) U.S. Cl. .................... 251/149.6; 604/256
(58) Field of Classification Search .............. 251/149.1, 251/149.4, 149.6, 149.7; 604/249, 256, 905
  See application file for complete search history.

(56) References Cited

U.S. PATENT DOCUMENTS

| 5,549,566 A | 8/1996 | Elias et al. |
| 6,039,302 A | 3/2000 | Cote, Sr. et al. |
| 6,050,978 A | 4/2000 | Orr et al. |
| 6,543,745 B1 | 4/2003 | Enerson |
| 6,609,696 B2 | 8/2003 | Enerson |
| 6,745,998 B2 | 6/2004 | Doyle |
| 6,964,406 B2 | 11/2005 | Doyle |
| 2002/0153503 A1* | 10/2002 | Newton et al. ........... 251/149.1 |
| 2003/0032940 A1 | 2/2003 | Doyle |
| 2003/0066978 A1 | 4/2003 | Enerson |
| 2003/0111623 A1 | 6/2003 | Enerson |
| 2003/0136932 A1 | 7/2003 | Doyle |
| 2004/0124389 A1 | 7/2004 | Phillips |
| 2004/0217315 A1 | 11/2004 | Doyle |
| 2004/0227120 A1 | 11/2004 | Raybuck |
| 2005/0087715 A1 | 4/2005 | Doyle |

FOREIGN PATENT DOCUMENTS

WO           98/17192        4/1998

OTHER PUBLICATIONS

International Preliminary Report on Patentability, corresponding to International Patent Application No. PCT/US2006/05153, dated Nov. 13, 2007.
European Search Report, corresponding to European Patent Application No. 06720733.2, dated Feb. 3, 2009.

* cited by examiner

Primary Examiner—John K Fristoe, Jr.
(74) Attorney, Agent, or Firm—Christopher J. Knors; Moore & Van Allen, PLLC

(57) ABSTRACT

A valved fluid connector reversibly attachable to a standard female connector and providing a flow channel between them comprising a tubular member, an elastic member surrounding at least a portion of the proximal end of the tubular member, the elastic member reversibly sealing the tubular member. When the valved fluid connector is engaged with a standard female connector device, the female connector urges the elastic member of the valved male connector into a stretched position to open the valve and permit fluid communication between the devices.

98 Claims, 21 Drawing Sheets

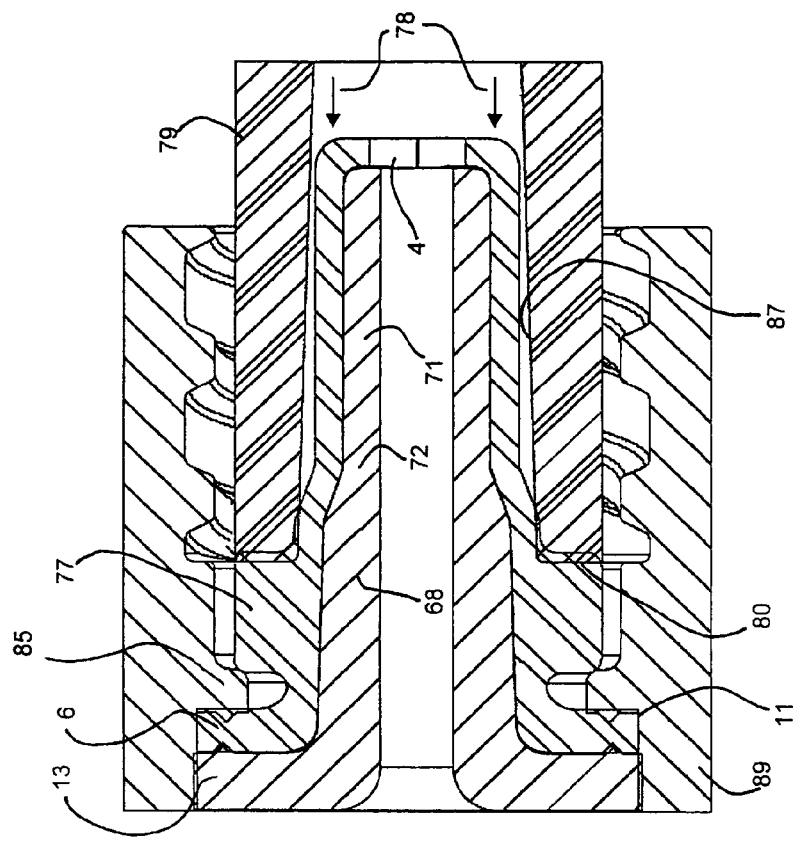
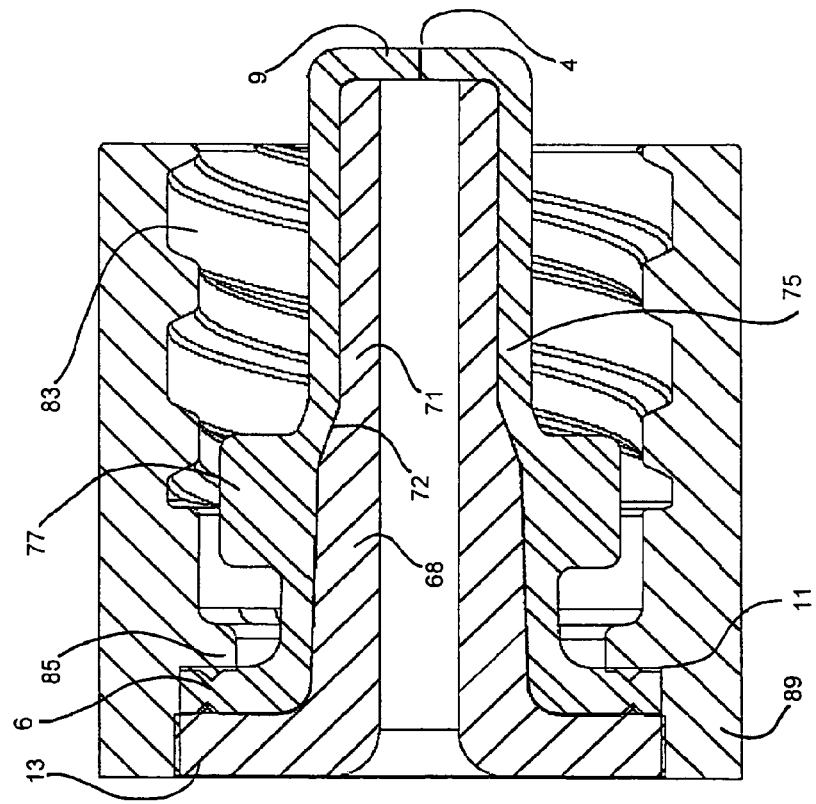
FIG. 10
FIG. 9

VALVED FLUID CONNECTOR

CROSS-REFERENCE TO RELATED APPLICATIONS

This application claims priority to U.S. Provisional Application No. 60/652,793, filed Feb. 14, 2005, and is incorporated herein by reference in its entirety.

FIELD

Disclosed herein is a valved fluid connector device, for example, a male luer connector that attaches to a female connector device such as, a female luer connector, to open a flow channel between the two devices. Engagement of the connector devices provides safe and efficacious medical fluid flow applications that are desirable for hospital, clinical, and laboratory use.

BACKGROUND

Medical male luer connectors have been standardized through ISO standard ISO-594-1 and 594-2. The geometry and use has been relatively unchanged for many years. However, the advent of communicable diseases transmittable by needle-sticks has driven multiple advancements on the female side of luer connectors. Injection sites and standard female luers have in many cases been replaced with "needle-free connectors"—i.e. female luers with an integrated valve. The valve is opened when a male luer is inserted into the device. When the male luer is removed, the valve closes. The needleless-device adaptation in healthcare continues to be driven by the need to reduce the number of needle sticks, and was accelerated by needle stick prevention legislation. Other benefits to needleless devices include reduction or total elimination of sharp components and systems that auto-close, keeping fluid path sterility in check.

Typical luer connections utilize a male luer connector that is inserted into a female luer connector. The male luer connector is typically threaded onto corresponding threads of the female luer connector to engage the two devices so that fluid may be passed between them without escaping or leaking from the connection.

Male luer components are adapted for use with multiple devices and procedures—such as chemotherapy, blood transfusion, and nuclear medicine. During these procedures with conventional luer devices, exposure to fluids—cytotoxic drugs, blood borne pathogens, radioactive drugs—may occur and result in serious consequences for the patient, caregiver, housekeeping staff, or any other individual who may come in contact with the fluids. Currently available male luer connectors when removed or inadvertently dislodged from its female connection may introduce substances to the atmosphere, leaking the drug or blood contents, and thereby exposing those individuals to the potentially harmful contents. The current process for removing a male luer from its fluidic system connection is to first clamp and then remove (as with an IV set), or just remove with extreme caution as to not drip or spill the fluid. This process is not automatic, leaves room for human error, and does not address the potential drops at the tip of the male luer even if the clamp is successfully used. Additionally, even if the fluid does not leak when the connectors are disengaged, the residual amount of fluid remaining on the tip of the connectors may still be harmful.

Previously described valved male luer connectors require an internal post that is provided by a specific type of valved female luer (such as the ICU Medical Clave needle-free valve) to protrude into the valved male luer. This greatly limits the ability for the device to work with multiple female luer and needle-free valves that are commercially in use.

The previously described male luer connectors may also require multiple valve components that are inserted inside the male body of the connector, thus complicating the manufacturing process due to space constraints within the male luer tip, and may limit the flow rate of the connector below that of the flow rate of a typical male luer.

Some previously described valved male connectors utilize metal springs that may make x-ray and MRI images unclear, and the stored kinetic energy of the spring may drive the valve component internal to the male luer toward the tip of the male luer and expel a small droplet or mist of fluid out of the tip upon disconnection.

Other previously described valved male connections include internal valve components downstream of the tip of the male connection just beyond its base. While flow rate through these devices may be acceptable, the tip of the male connector is left exposed to the environment, keeping the patients and clinicians at risk of exposure to droplets or mists that may easily be expelled from within the void volume of the male connector tip itself. These designs also suffer from having multiple components, adding complexity and cost to assembly, and may contain metal springs that may make x-ray and MRI images unclear. Additionally, these designs are not swab-able.

Other previously described self-sealing male connectors may be limited in their compatibility with existing needle-free valves on the market. For example, some valved male luer connector designs may be compatible with some female valves (such as SmartSite) with no internal protruding post. However, use with female connectors with internal posts would geometrically prohibit the insertion of the internal posts into smaller diameter holes of the male tip, likely resulting in damage to one or both of the devices, potentially rendering either unusable. In addition, the post within some of the previously described self-sealing male connector designs protrudes through the elastic member, causing a "squeegee effect" on the internal post of the device, leaving potentially harmful fluid droplets on the tip upon its disconnection.

Additionally, other previously described self-sealing male luer connectors with biased valve plugs would be inherently unattractive in both their incompatibility with some needle-free valves on the market and in their low flow rates through the device. These devices would not be compatible with many needle-free valves having internal posts (such as the ICU Medical Clave needle-free valve) as the post would be geometrically prohibited from insertion into the ID of the male connector tip. This would likely damage one or both devices, perhaps rendering one or the other unusable.

By redesigning the standard male luer connector to be a valved male connector capable of completely shutting off flow at the tip of the male connector with no restrictions within the male luer itself, the problems listed above may be avoided. Additionally, if the male luer connector may be adequately disinfected by swabbing prior to connecting or between connections, it may eliminate any need for a cap to be used—an extra component that adds cost and often becomes lost. Finally, by automatically shutting off upon disconnection, the underlying fluid path sterility may be more readily maintained, whereas it would otherwise be exposed to the environment.

Therefore, disclosed herein is a more universally compatible valved male connector that securely contains the fluid materials included therein when engaged to a standard female luer or needless connector. There is also disclosed a valved male connection that, when disengaged, seals off the male connector so that users of the connector are protected from hazardous drugs that might otherwise remain on, or just inside, the connector tip surface.

SUMMARY OF THE INVENTION

Valved fluid connectors described herein include a valved fluid connector for engagement with a female connector for use with an intravenous line (IV), syringe, blood collection or other fluid-type connections.

In one embodiment, a valved male connector for providing fluid flow comprising: a tubular housing having an outer surface and an inner surface, a proximal end and a distal end, the proximal end engagable with a female connector; a tubular member positioned within the housing comprising: an axial conduit between a proximal end and a distal end; an outer surface; and an internal wall element forming an upper and lower opposing conduit, the wall element bisecting the axial conduit into an upper and lower axial conduit; an elastic member comprising: a forward and a rearward end; a flange section positioned at the reward end securable within the tubular housing; a first laterally protruding sliding seal on the interior surface of the elastic member adjacent the exterior surface of the tubular member; an interior surface portion having a diameter larger than the diameter of the tubular member exterior surface positioned forwardly from the first laterally protruding sliding seal; a valve member integral with the forward end and in sealing relationship with the proximal end of the tubular member; and a movable conduit defined by the first laterally protruding sliding seal, the interior surface portion and outer surface of the tubular member; and an annular collar located within the housing between the elastic member and the tubular housing and in contact with the flange section, the annular collar slidably movable between the tubular housing and the elastic member, is disclosed.

During engagement with a female connector the annular collar is urged rearward, stretching the elastic member flange section and urging the movable conduit over at least a portion of the axial and opposed conduits and the internal wall element allowing fluid communication between the conduits and through the tubular member while concurrently opening the valve member. Upon disengagement with the female connector the annular collar and movable conduit are urged forward by the relaxing flange section, ending fluid communication between the axial and opposed conduits and through the tubular member, while concurrently closing the valve member.

In another embodiment, a fluid connector comprising: a housing; an elastic member comprising a forward end integral with a valve member and a rearward end comprising a flange secured within the housing; a tubular member with a proximal end positioned within the elastic member; the proximal end of the tubular member in sealing relationship with the valve member of the elastic member and a distal end secured to the housing; an annular collar member located between the housing and the elastic member and in contact with the flange, the annular collar member slidably movable between the housing and the elastic member; wherein the annular collar member is urged rearwardly from the tubular member proximal end stretching the elastic member and opening the valve member, is disclosed. When the female connector is engaged to the valved male connector, for example, as described above, the housing of the female connector urges the annular collar rearwardly. This urges the elastic member into a stretched position, reversibly opening the valve member and unsealing the proximal end of the tubular member to allow liquid flow between the two connectors.

In another embodiment, a valved male connector comprising: a housing; a tubular member contained within the housing with a proximal end and a distal end, a first stepped area and a second stepped area positioned forwardly of the first stepped area defining a first groove; an elastic member comprising: forward and rearward ends; an interior and exterior surface, the interior surface adjacent the tubular member; at least one lateral protrusion on the exterior surface; and a valve member at the forward end of the elastic member and in reversible sealing relationship with the proximal end of the tubular member, is disclosed.

In another embodiment, a valved male assembly comprising: a tubular portion comprising: a proximal end; and a first stepped area and a second stepped area positioned forwardly from the first stepped area forming a groove; an elastic member comprising: a forward end surrounding the proximal end of the tubular portion; and a rearward end surrounding at least a portion of the groove but not secured to the distal end of the tubular portion; laterally extending protrusions positioned between the forward and rearward end; and a valve member at the forward end of the elastic member, the valve member in sealing relationship with the proximal end of the tubular portion; wherein sealable engagement with a female connector contacts the laterally extending protrusions urging the elastomeric member into a stretched position opening the valve member, is disclosed.

In yet another embodiment, a valved fluid connector comprising: a tubular member having a distal end, a proximal end and a stepped area spaced distally from the proximal end; an elastic member comprising: inner and outer surfaces; laterally extending protrusions projecting from the outer surface; and opposite rearward and forward ends, the forward end surrounding the proximal end of the tubular member and the rearward end surrounding a portion of the stepped area of the tubular member, wherein the rearward end of the elastic member and the distal end of the tubular member are unattached; and a valve member at the forward end of the elastic member, the valve member in sealing relationship with the proximal end of the tubular member, is disclosed.

In yet another embodiment, a method for improving human safety during manipulation or transfer of fluid or chemical agents comprising: providing contact of a fluid or chemical agent with a valved male connector, the valved male connector comprising: a housing; an elastic member comprising a forward end integral with a valve member and a rearward end comprising a flange secured within the housing; a tubular member with a proximal end positioned within the elastic member; the proximal end of the tubular member in sealing relationship with the valve member of the elastic member and a distal end secured to the housing; and an annular collar member located between the housing and the elastic member and in contact with the flange, the annular collar member slidably movable between the housing and the elastic member; and b) transferring or manipulating the fluid or chemical agent, is disclosed.

BRIEF DESCRIPTION OF THE DRAWINGS

The present invention will be better understood from the following detailed description of various exemplary embodiments of the invention, taken in conjunction with the accompanying drawings in which like reference numerals refer to like parts and in which:

FIG. 9 is a side cut-away view of alternate tubular member and elastic member components of FIG. 8 of one embodiment of the valved fluid connector;

FIG. 10 is a side cut-away view similar to FIG. 9 showing a female connector and the valved fluid connector engaged;

DETAILED DESCRIPTION OF THE EMBODIMENTS

The valved fluid connectors described herein may be considered advantageous for many reasons. The valved fluid connector may be a male-type connector. The valve contained on the end of the valved male connector is self-closing so that it ensures that minimal amounts of fluid remain on any exposed surface of the connector. When the valved male connector is disengaged from an appropriate female connector, the male connector seals off to protect any user from exposure to potentially hazardous fluids. This helps ensure hazardous or highly toxic drugs, such as those used in chemotherapy treatments, are substantially non-existent on the surface of the male connector. Also, bodily fluids, such as blood, are substantially non-existent on the surface of the connector thus minimizing exposure to potentially diseased blood. The valved connector embodiments described herein allow either mutual swabbing or one-sided swabbing because there are minimal crevices on the connector and the valve member is substantially flush or extended.

Figure 1:
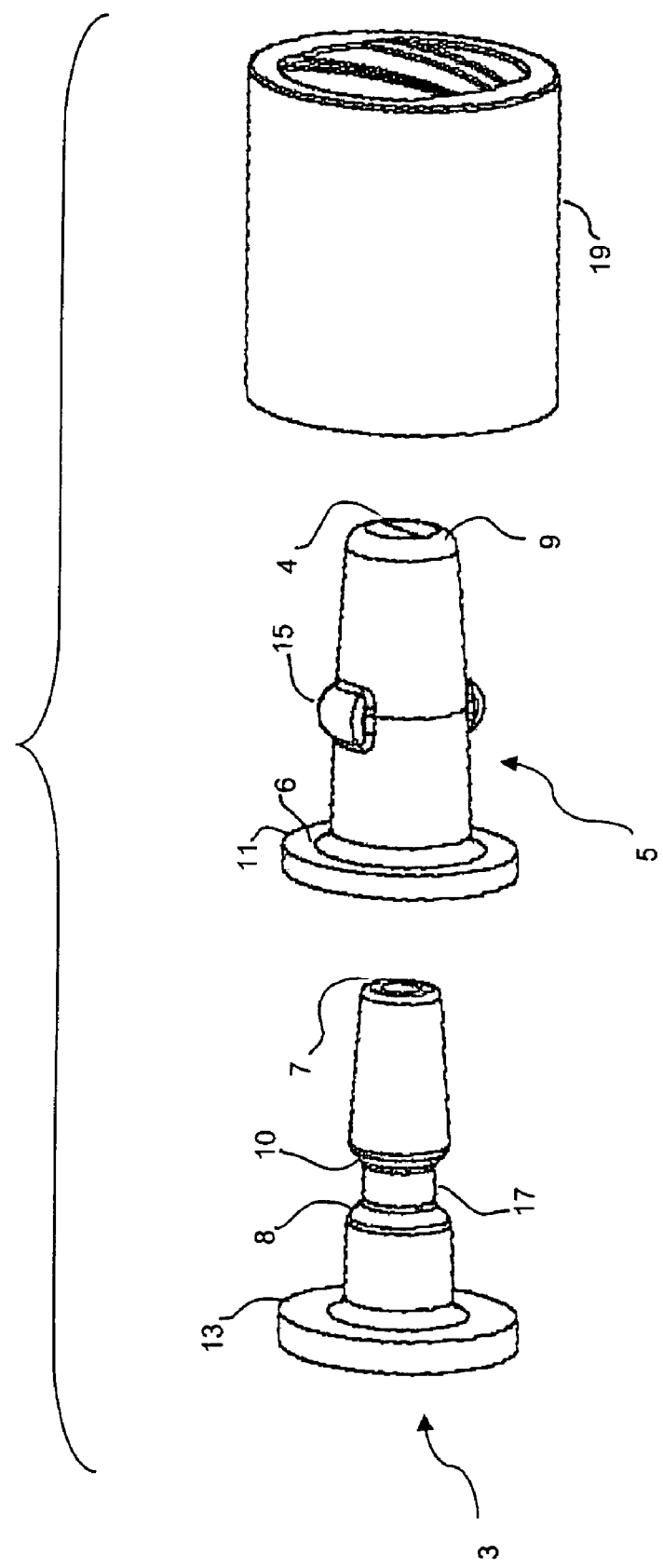
FIG. 1 is an exploded view of the components of one embodiment of the valved fluid connector.
Figure 2:
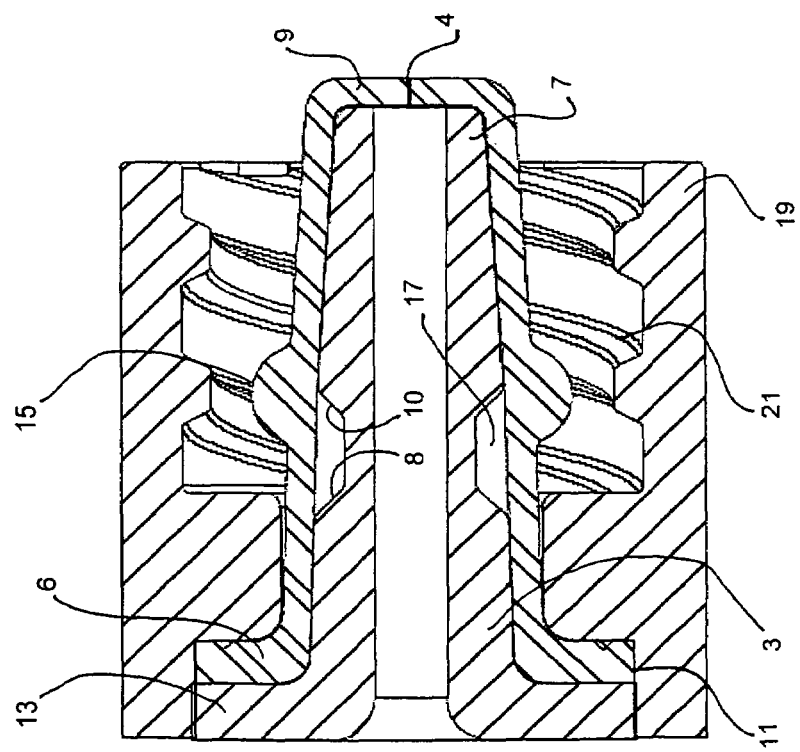
FIG. 2 is a side cut-away view similar to FIG. 1 of the male connector.

Referring to FIGS. 1 and 2, a valved male connector comprises a tubular member 3 having a flange 13 and elastic member 5. First stepped area 8 and second stepped area 10 positioned forwardly of the first stepped area form groove 17. The elastic member surrounds the proximal end 7 of the tubular member. The elastic member has valve member 9 comprising a sealing slit 4 that opens and closes access through the proximal end of the tubular member. Base 6 of the elastic member abuts the flange 13 of the tubular member forming lower seal 11. Elastic member 5 comprises laterally extending lugs 15 positioned approximately midway between valve member 9 and lower seal 11 and is at least partially forward of groove 17. Lug 15 may be of annular shape or other suitable shape. Groove 17 receives the lugs 15 upon stretching of the elastic member. Lugs 15 are positioned approximately 90 degrees to the direction of slit 4 to assist with biasing the slit open. Groove 17 may be symmetrically or unsymmetrically tapered, circularly cut, or may be square cut. The tubular member and elastic member are secured or integrated with housing member 19. Housing member component 19 secures the lower seal 11 to the base 13 of the tubular member.

Alternatively, elastic member 5 may be directly attached to the tubular member flange without a housing member. Attachment may be, for example, by adhesive, welding, solvent bonding or snap-fit, for example. Housing member 19 includes threaded attachments elements 21 for engaging compatible female connectors and protrusions 22 for limiting the depth of insertion of a female connector and/or the transit of lugs 15. Seal 11 is abutted to base 13 by protrusion 22.

Figure 3:
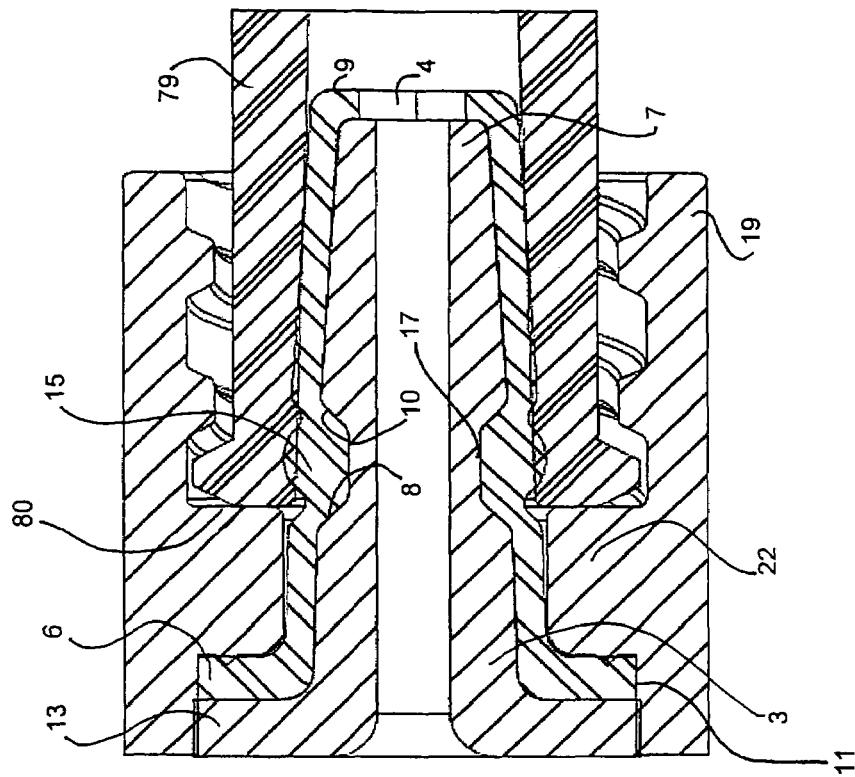
FIG. 3 is a side cut-away view similar to FIG. 2 showing a female connector and the valved fluid connector engaged.

Referring to FIG. 3, upon engagement of the above described valved male connector with a surface 80 of female connector 79, lug 15 is translated in a direction opposite the proximal end and elastic member sidewall 16 is stretched in a direction opposite the proximal end 7 (as indicated by arrows 20) and is received by annular groove 17 opening slit 4 of valve member 9 and permitting fluid communication between the connectors. Translocated lugs 15 may provide additional sealing and retainment for the two connectors during engagement and use. When the valved male connector is disengaged from a female connector, the opening of valve member 9 of elastic member 5 is closed, sealing off the open end of tubular member 3.

Figure 5:
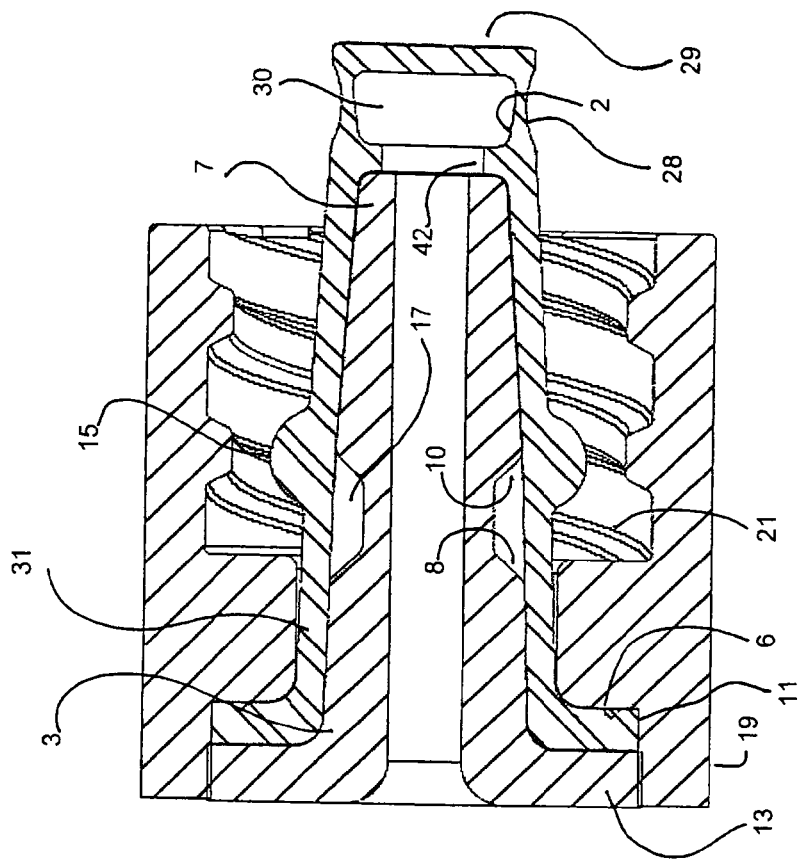
FIG. 5 is a side cut-away view of the tubular member and elastic member components of one embodiment of the valved fluid connector.
Figure 4:
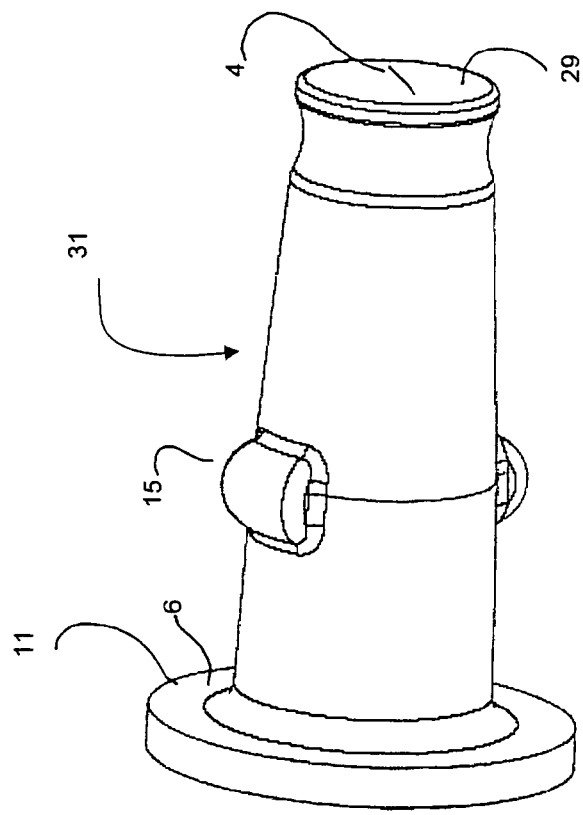
FIG. 4 is a prospective view of the elastic member of one embodiment of the valved fluid connector.

Referring to FIGS. 4 and 5, an alternative arrangement of the valve member of the previous embodiment is illustrated. Elastic member 31 tapers in conformity with and surrounds tubular member 3 with alternate valve member 29 having a thinned reverse tapered annular section 28 extending slightly forward of tubular member proximal end 7 forming a gap 30. Lateral inward annular projection 42 is positioned on the inside wall surface 2 of elastic member 31. In this configuration, valve member 29 will start opening upon contact with a female connector. When contact is made, the valve member 29 of elastic member 31 is urged rearwardly from proximal end 7 of the tubular member 3, exerting a radial elongational tension to the surface urging valve member 29 to open slightly prior to threaded elements of the female connector engaging lugs 15. Upon full engagement of the threaded elements, this embodiment functions the same as the previous embodiment.

Upon engagement and axial loading by a needle-free valve, for example, pressure is exerted to the surface 29 of elastic member 31, urging slit 4 to start opening due to resistance of projection 41 transiting tubular member proximal end 7 radially expanding slit 4 prior to full engagement with female connector. This design may assist with valve opening, which may otherwise be hindered by the pressure between the elastic member 31 surface 29 and the mating surface of the needle-free valve. In addition, user may experience a tactile feel upon seal 41 releasing from proximal end 7, indicating engagement of the connectors.

Figure 7:
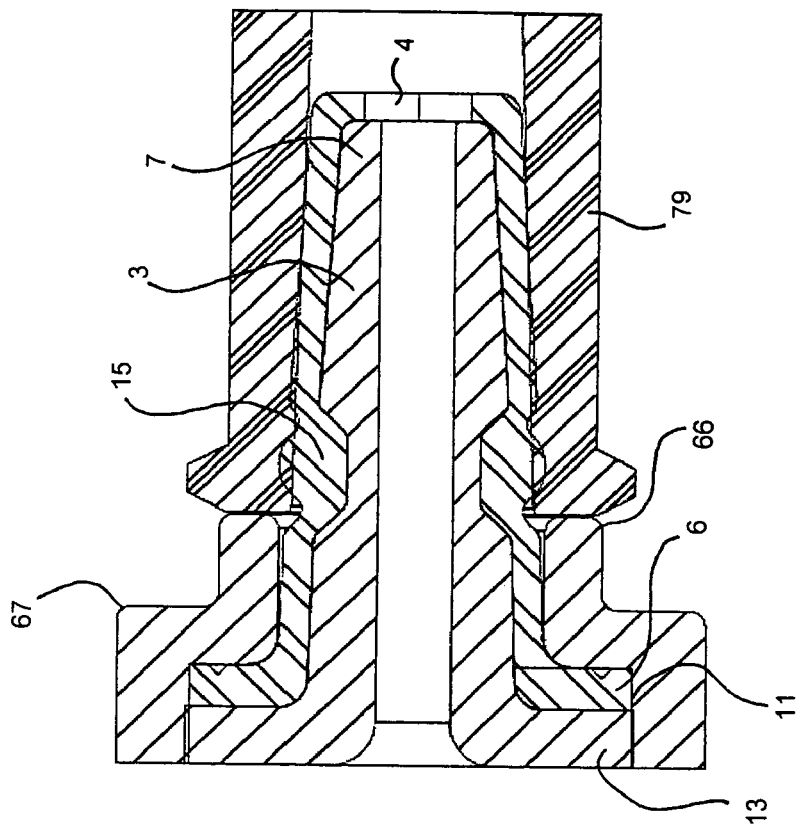
FIG. 7 is a side cut-away view similar to FIG. 6 showing a female connector and the valved fluid connector engaged.
Figure 6:
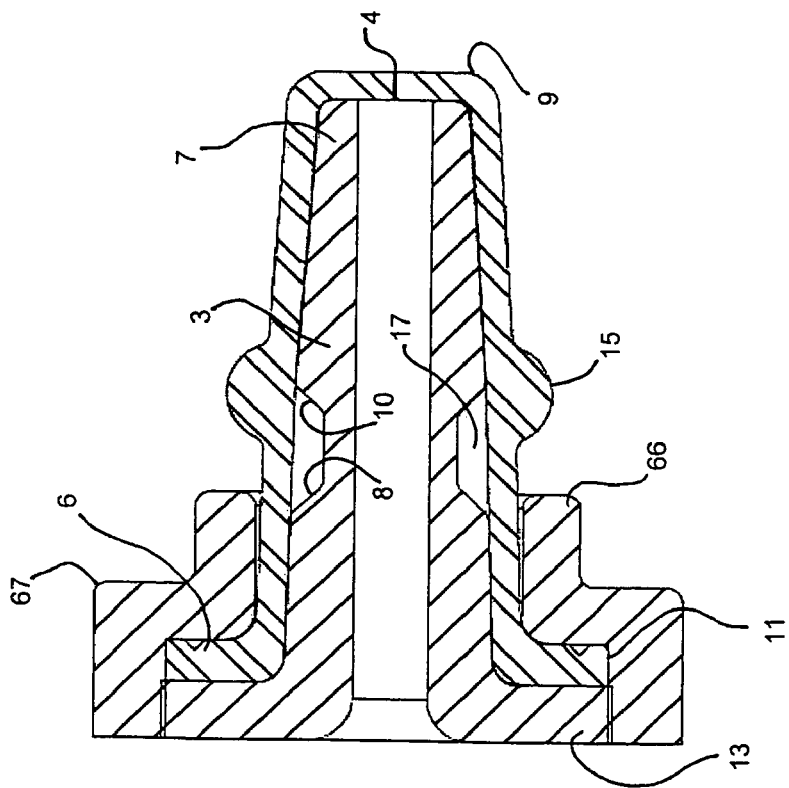
FIG. 6 is a side cut-away view similar to FIG. 5 of the tubular member and elastic member components of one embodiment of the valved fluid connector.

Referring to FIGS. 6 and 7 another alternative arrangement of the previous embodiment of FIG. 1 is illustrated. This embodiment functions the same as the embodiment of FIG. 1 except that the threaded attachment elements are replaced with a retaining ring 67 of housing 67 for "slip-luer" engagement with female housing element 59. Forward projecting collar 66 of housing 67 provides depth-limiting means for the female connector. Upon engagement, retaining ring 67 urging of lugs 15 into groove 17 may provide tactile indication to a user of successful connection of the devices.

Figure 8:
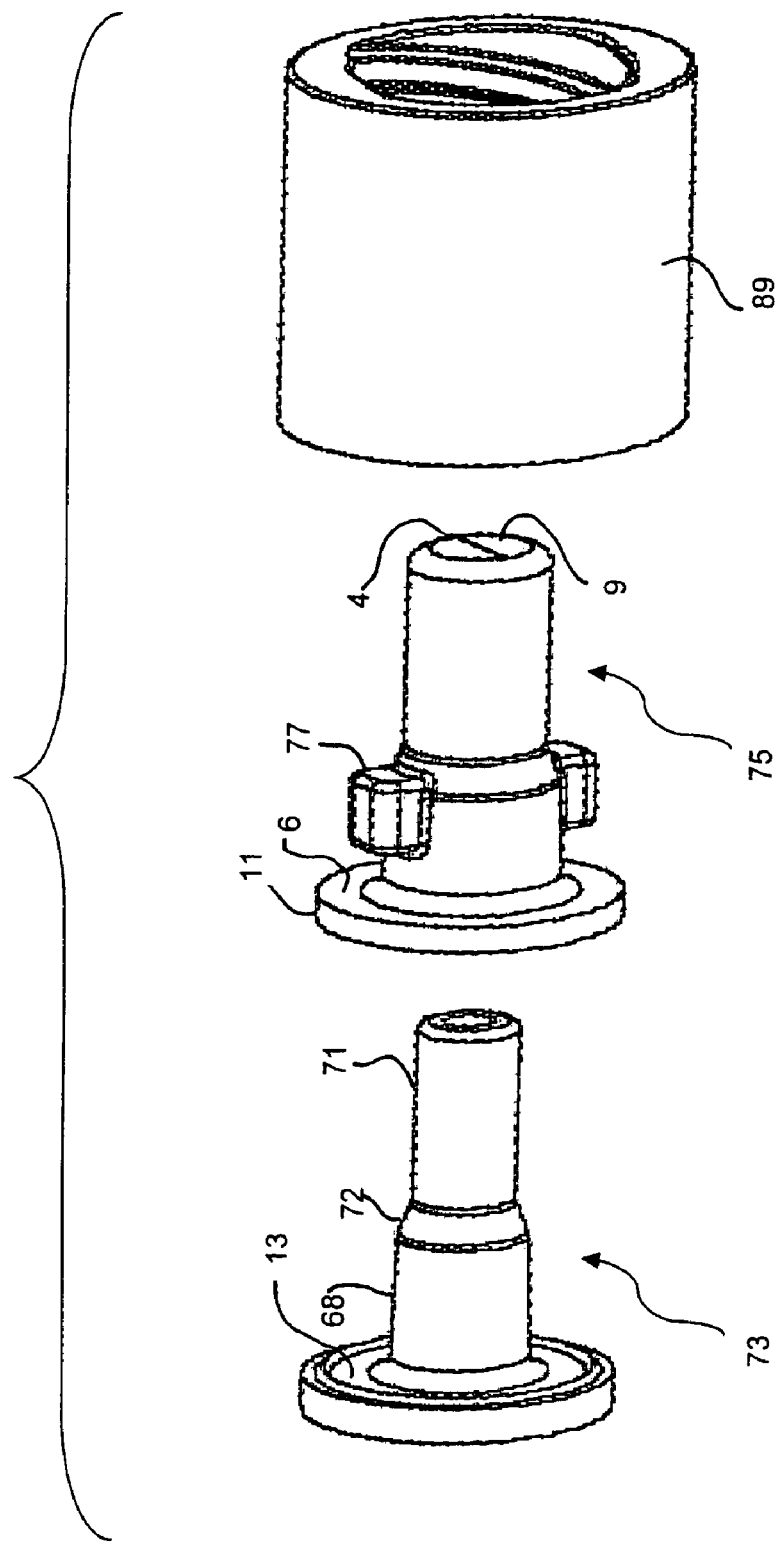
FIG. 8 is an exploded view of an alternate valved fluid connector with alternate elastic member and tubular member component.

Referring to FIGS. 8-10, alternate embodiments of the tubular member and elastic member are illustrated. Referring to FIGS. 8-10, tubular member 73 has a stepped area 72 forming larger diameter lower section 68 and smaller diameter upper section 71 projecting forwardly from the lower section 68. Tubular member 73 upper section 71 and at least a portion of lower section 68 are surrounded by conforming elastic member 75 having base 6 abutting base 13 of tubular member forming seal 11. Elastic member 75 has laterally projecting lugs 77 positioned at least partially in stepped area 72 and forward of base 6, which forms lower seal 11. Lugs 77 may be of a single annular shape or other suitable shape. Housing component 89 has threaded elements 83 and inwardly facing protrusion 85. Protrusions 85 may comprise a plurality of projections or a single annular projection. Upon engagement of female connector 79, face 80 of the female connector 79 contacts lugs 77 stretching elastic member 75 (as indicated by arrows 78) and opening slit 4 of valve member 9. Optionally, tubular member may contain additional stepped areas and grooves (not shown) to receive lugs 77 during engagement with female connectors. Protrusion 85 of housing component 89 secure elastic member 75 provides depth-limiting means for the female connector and may optimize opening of valve member 9 or prevent over tightening or damage to valve. Stepped area 72 and larger diameter lower section 68 engage with inside surface of female connector 87, while smaller diameter lower section 71 provide clearance to allow for stretching of elastic member 75.

Figure 12:
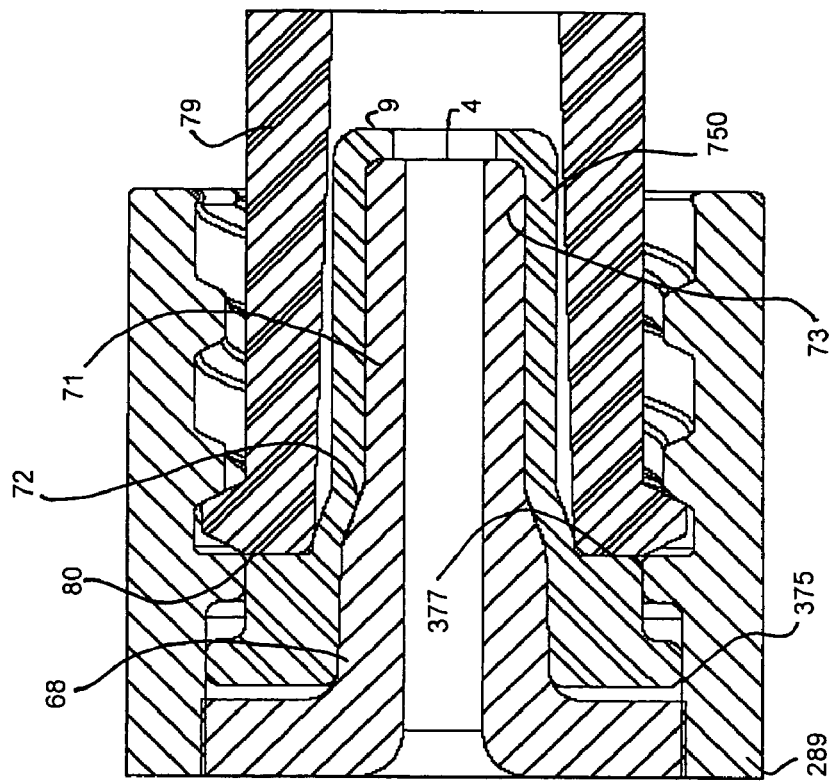
FIG. 12 is a side cut-away view similar to FIG. 11, showing a female connector and the valved fluid connector engaged.
Figure 11:
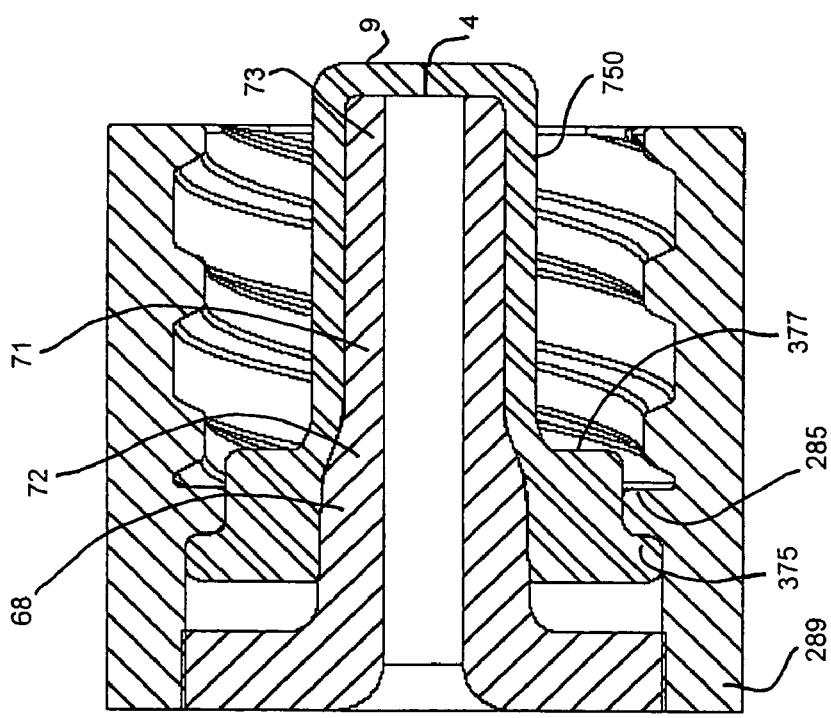
FIG. 11 is a side cut-away view of alternate tubular member and elastic member components of one embodiment of the valved fluid connector.

An additional embodiment where the elastic member is not secured to or retained by the base of the tubular member is shown in FIGS. 11 and 12. Alternative elastic member 750 surrounding tubular member 73 has first stepped lateral protrusion 377 which functions as lug to stretch elastic member upon engagement with female connector surface and second stepped lateral protrusion 375. Protrusion 377 may be annular or of any other shape. Housing component 289 having inward protrusion 285, positioned between the first and second stepped protrusions 377 and 375, secures elastic member in housing component 289 and may also function as depth-limiting means for female connector surface 80 and/or stretch of elastic member 750. Optionally, upon assembly, inward protrusion 285 of housing component 289 may slightly pretension elastic member 750 to provide a seal between the elastic member and the housing. Upon engagement by female connector surface 80 urges second stepped protrusion 377 rearwardly, stretching elastic member 750 and activating valve member 9. Distal sealing between elastic member 750 and tubular member section 68 is accomplished with interference of interior surface of protrusion 377.

Figure 13:
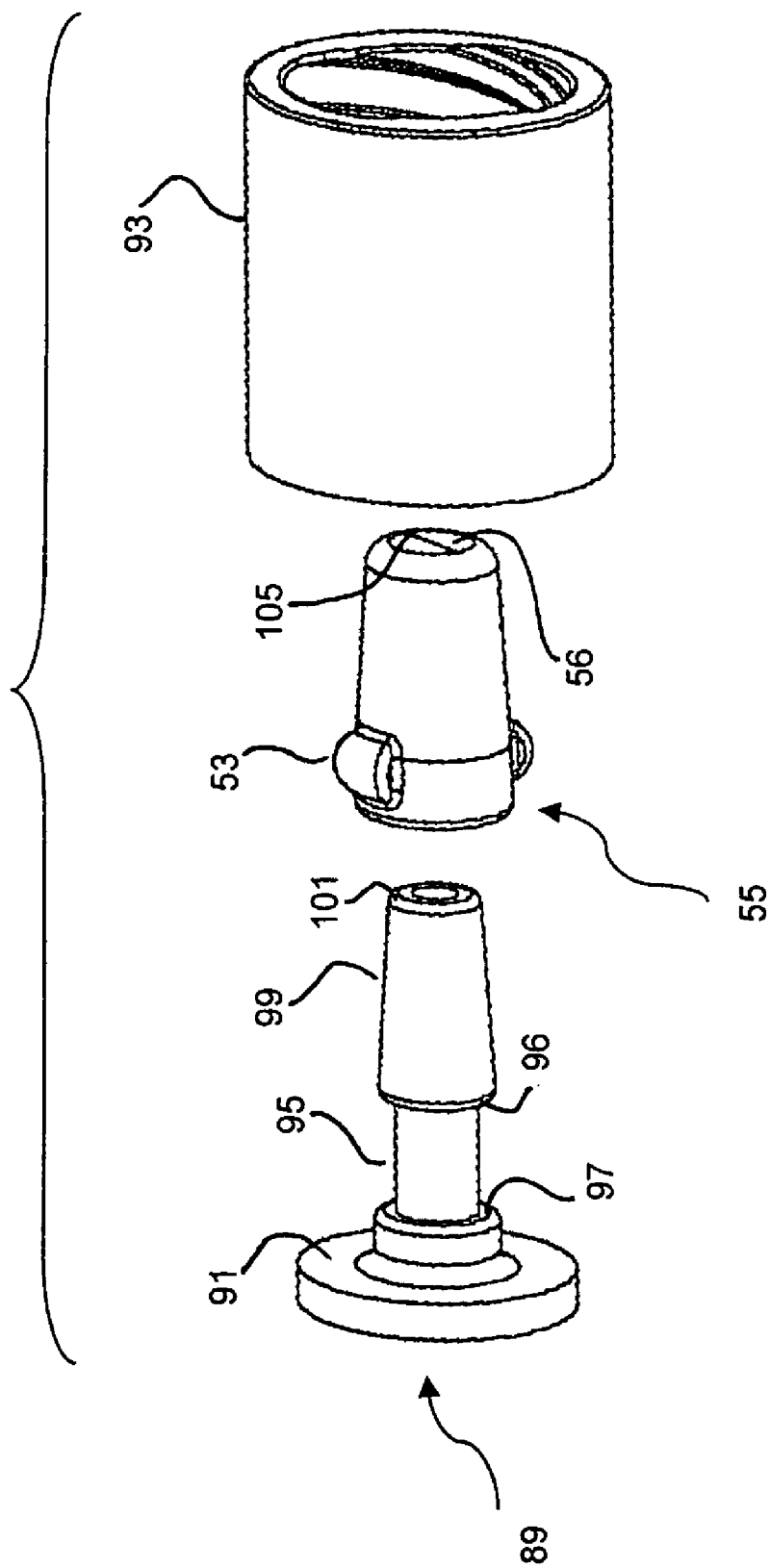
FIG. 13 is an exploded view of an alternate valved fluid connector with alternate elastic member and tubular member component.
Figure 15:
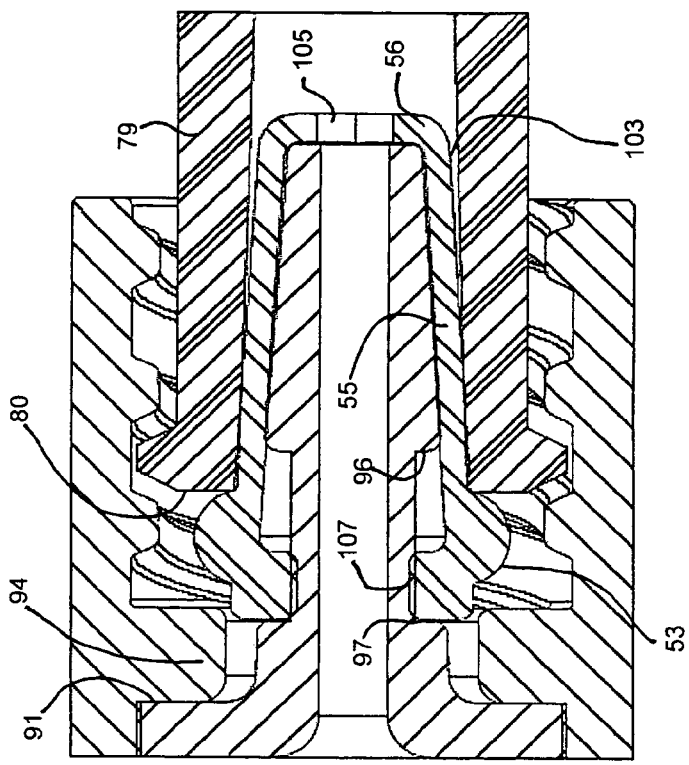
FIG. 15 is a side cut-away view similar to FIG. 14, showing a female connector and the valved fluid connector engaged.
Figure 14:
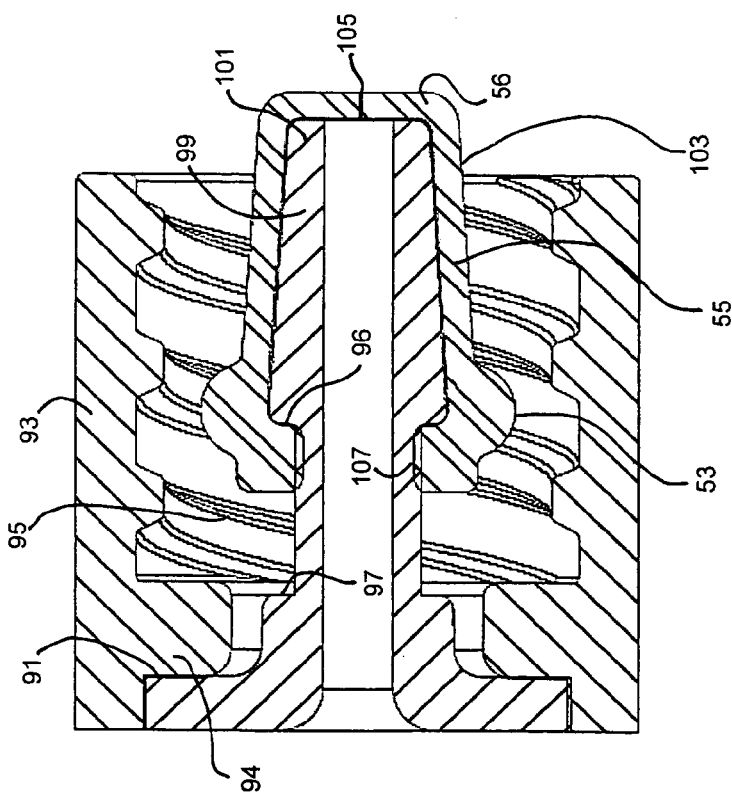
FIG. 14 is a side cut-away view of alternate tubular member and elastic member components of FIG. 13.

Referring to FIGS. 13-15, another alternate embodiment is illustrated whereby the elastic member is not secured to or retained by the base of the tubular member. Thus, tubular member 89 has first stepped area 97 and second stepped area 96 positioned forwardly of the first stepped and rearwardly of proximal end 101 forming groove 95 and upper section 99 and lower section 97. Elastic member 103 surrounds the upper section of tubular member 99 and at least a portion of groove 95 without being secured to or retained by base 91 of the tubular member 89. Slit 105 of valve member 56 is in reversible sealable relationship with the proximal end 101 of tubular member 89. Sliding interference seal portion 107 is positioned in groove 95 of tubular member 89. In this arrangement seal portion 107 is sealably and slidably engaged with grove 95, while retained on tubular member 89. Lugs 53 extend laterally outward from tubular member 89. Lug 53 may be a single annular in shape or comprise a plurality of lateral protrusions of any suitable shape. Preferably lugs 53 are positioned approximately 90 degrees of the direction of slit 105 to optimize slit opening. Protrusion element 94 of housing component 93 secures base 91 of tubular member 89 without securing or retaining elastic member 103 to base 91.

Upon engagement with face 80 of female connector 79, lug 53 is urged axially and slidably received by the grove 95, stretching elastic member 103 and causing reversibly sealable slit 105 to open allowing fluid communication between the connectors. When substantially engaged with the female connector, lug 53 may provide additional sealing engagement between the connectors. Optionally, female connector may also frictionally engage the outer sidewall of elastic member 103 to assist in sealing, retainment of female connector, and the actuation of slit opening. Optionally, housing 93 and female connector 79 may be of the slip luer design (without threaded elements, not shown) as described above. Protrusion element 94 and/or first stepped area 97 provide depth-limiting means for the lugs 53 and seal portion 107 and may optimize valve 56 opening and/or prevent over tightening or damage to the valve. Upon disengagement with the female connector, seal portion 107 stops reverse transiting of elastic member 55 by contacting stepped area 96.

Figure 16:
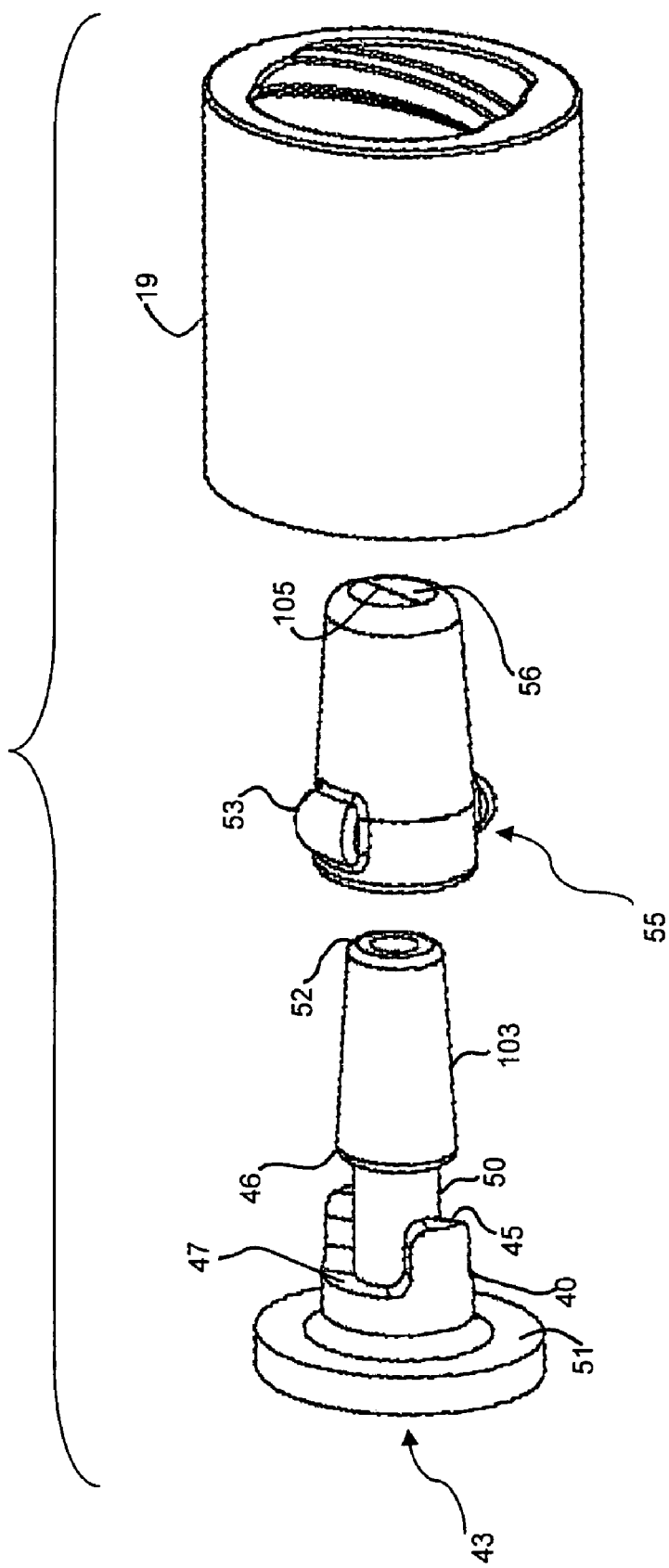
FIG. 16 is an exploded view of an valved fluid connector with alternate elastic member and tubular member component.
Figure 18:
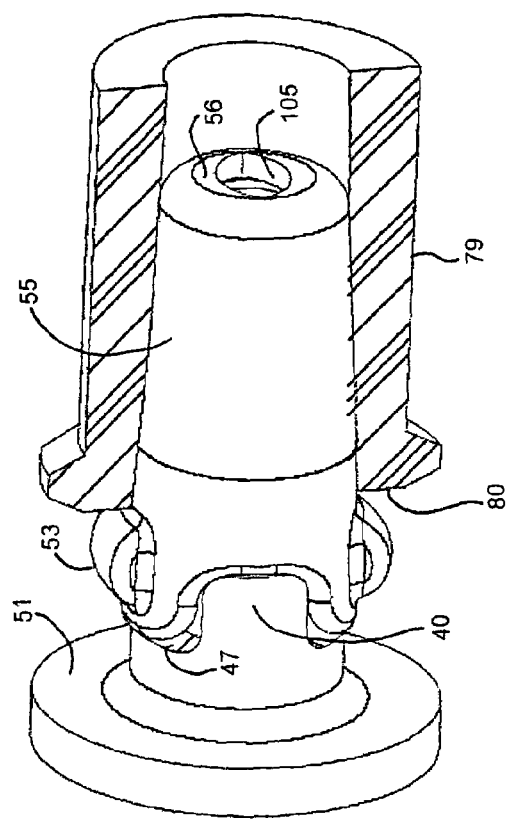
FIG. 18 is a prospective view similar to FIG. 17, with the female connector engaged.
Figure 17:
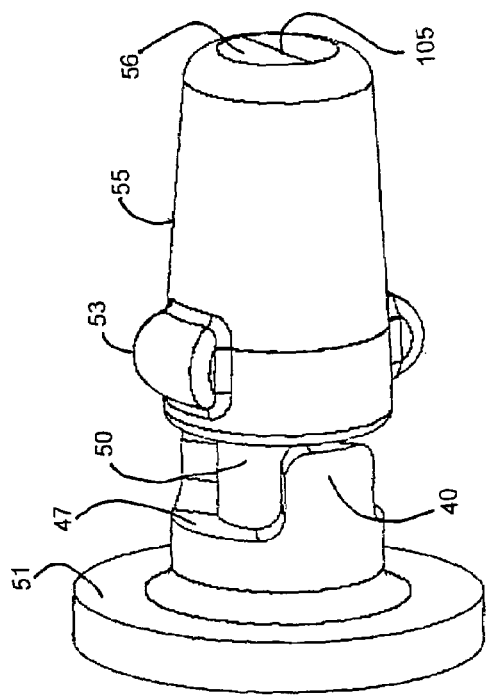
FIG. 17 is a partial cut-away view showing an alternate tubular member and elastic member embodiment.

Referring to FIGS. 16-18, another alternative embodiment is illustrated whereby the elastic member is not secured or retained to the base of the tubular member. Tubular member 43 has first stepped area 45 and second stepped area 46 positioned forwardly of the first stepped and rearwardly of proximal end 52 forming groove 50, upper section 103 and lower section 40. Lower section 40 has recessed areas 47 to receive lug 53 of elastic member 55. Upon engagement with a female connector 57, lugs 53 are urged rearward in recess areas 47 stretching elastic member 55 and opening slit 105 of valve member 56. Upon disengagement lugs 109 are returned to a generally unstretched state and allow valve member slit 105 to close. Housing element 19 is securable to tubular member base 51 and partially contains elastic member 55.

Figure 19:
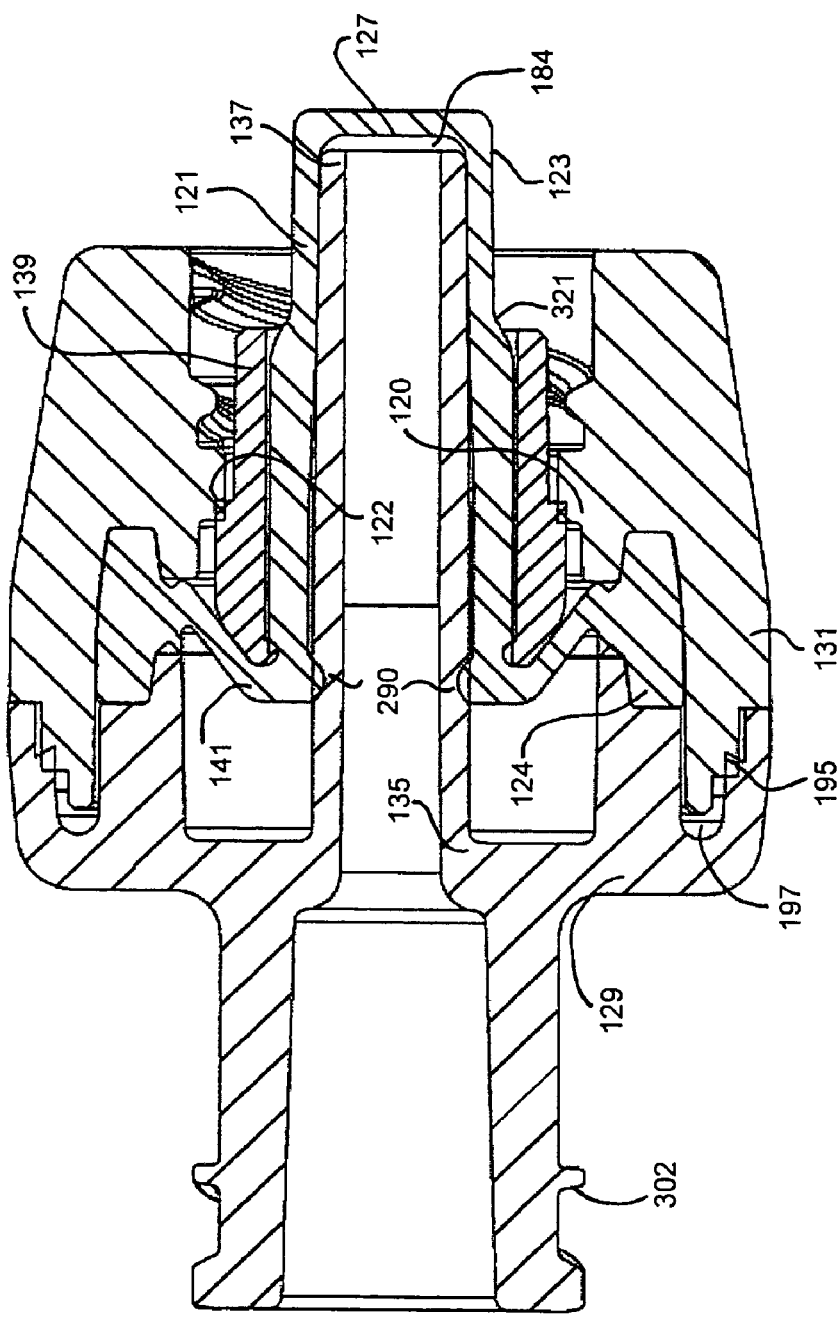
FIG. 19 is a side cut-away view showing an alternative valved fluid connector embodiment.
Figure 20:
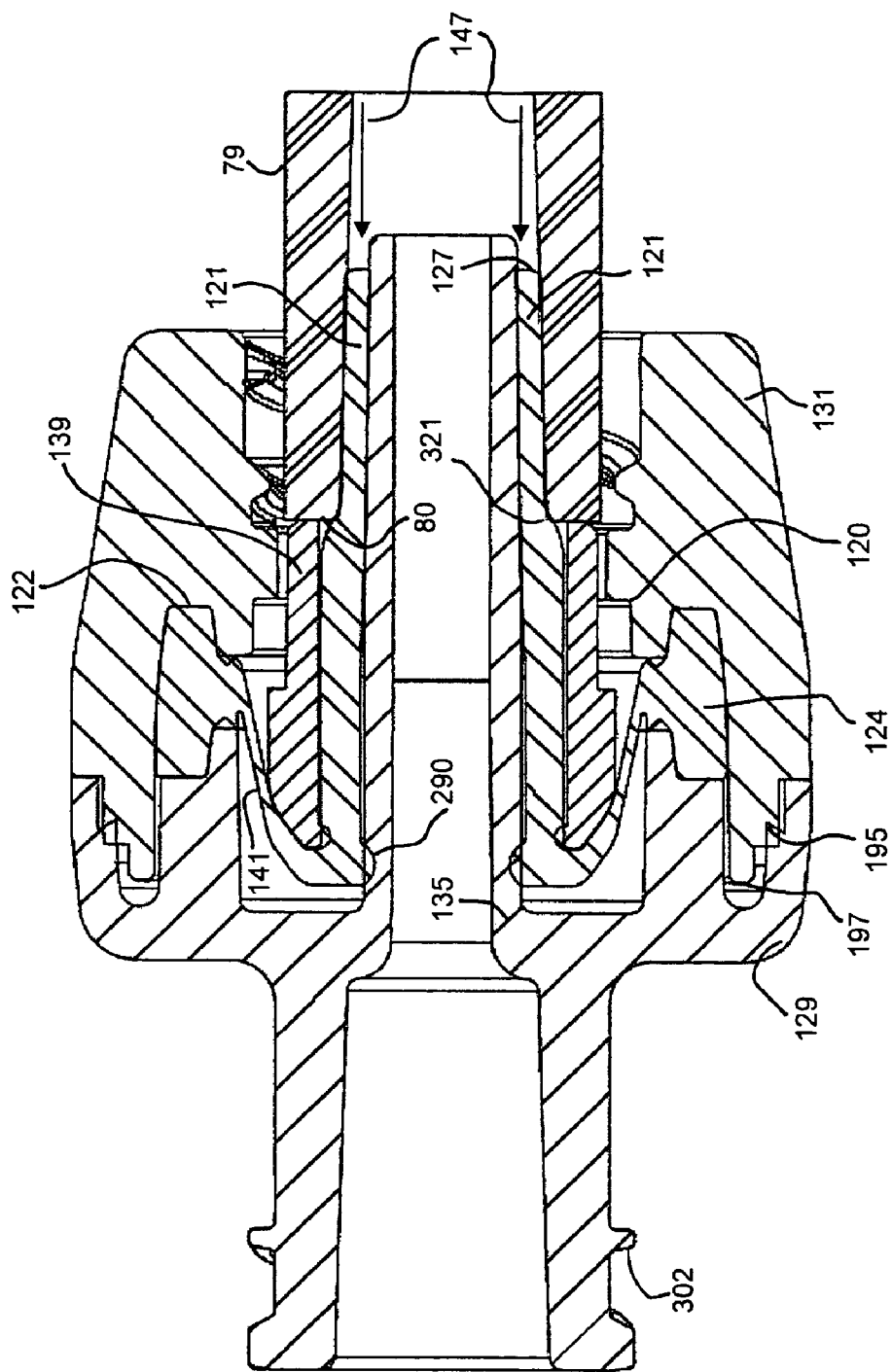
FIG. 20 is a side cut-away view similar to FIG. 19 showing an alternative valved fluid connector embodiment and female connector engaged.
Figure 21:
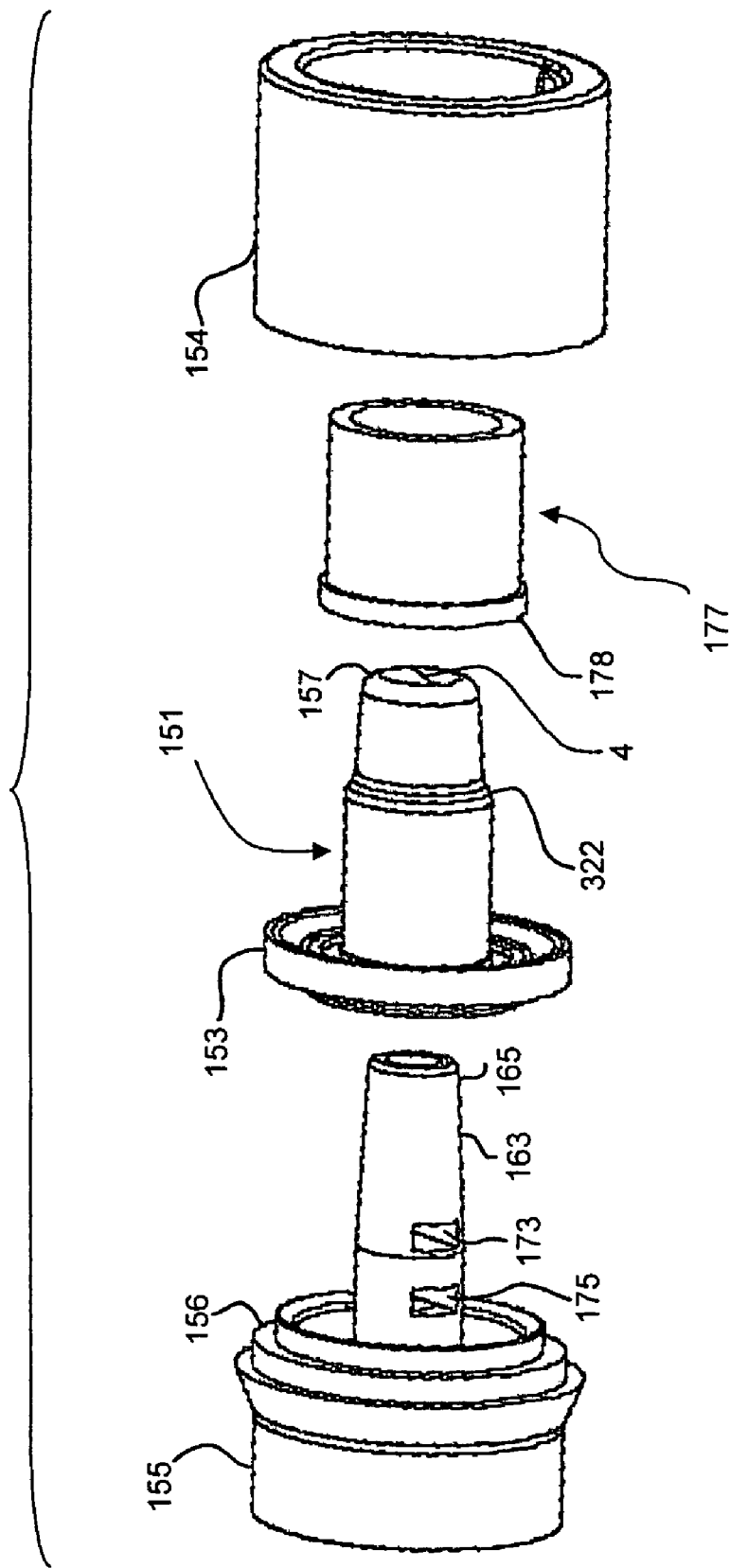
FIG. 21 is an exploded view showing an alternative valved fluid connector embodiment.
Figure 22:
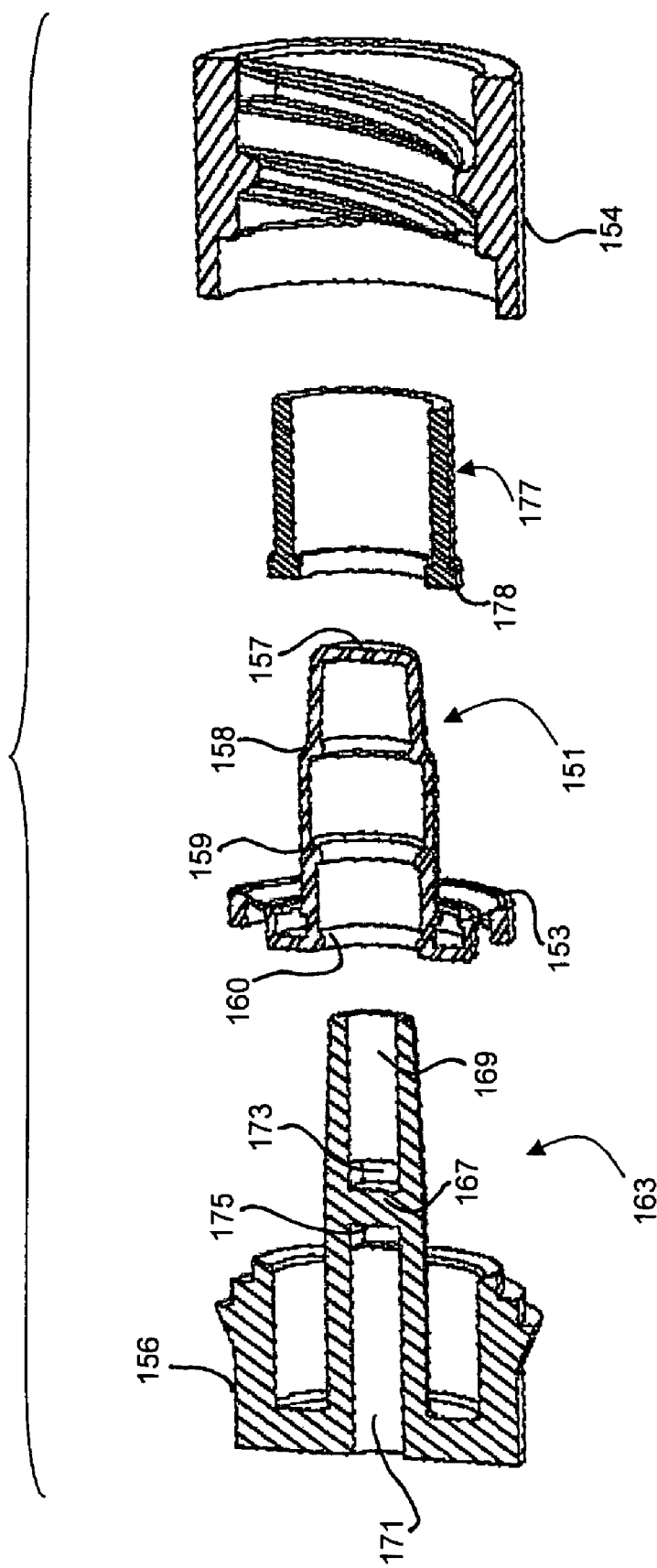
FIG. 22 is an exploded cut-away view similar to FIG. 21, showing an alternative valved fluid connector embodiment.

FIGS. 19 and 20 illustrate another embodiment of a valved male connector comprising a housing, a tubular member, an elastic member and a movable annular collar. Elastic member 121, having a forward end 123 and rearwardly positioned flange 124, is secured between lower housing component 129 and upper housing component 131, suspending membrane section 141 of flange 124. Proximal end 137 of tubular member 135 is positioned within and at least partially surrounded by elastic member 121. Proximal end 137 is in sealable relationship with valve member 127. Annular collar 139 is positioned between the housing 125 and the elastic member 121 and in contact with membrane 141. Reduced diameter interference element 120 of upper housing component 131 secures collar 139 by contacting laterally extending lip 122 of collar 139 and provides for depth-limiting means for the female connector. Stepped area 321 of elastic member provides sealing means during engagement with female connector. Step area 321 also may provide improved valve member actuation and reseal as well as desirable tactile properties for the user. Gap 184 assists valve member actuation, in particular, with engagement by female connectors comprising posts.

When the female connector 79 engages the valved male connector, the forward surface 80 of the female connector engages collar 139 and urges the collar rearwardly. This urges membrane 141 and elastic member 121 into a tensioned or stretched position (as indicated by arrows 147) opening valve member 127 reversibly unsealing the proximal end of the tubular member to allow liquid flow between the two connectors.

Figure 23:
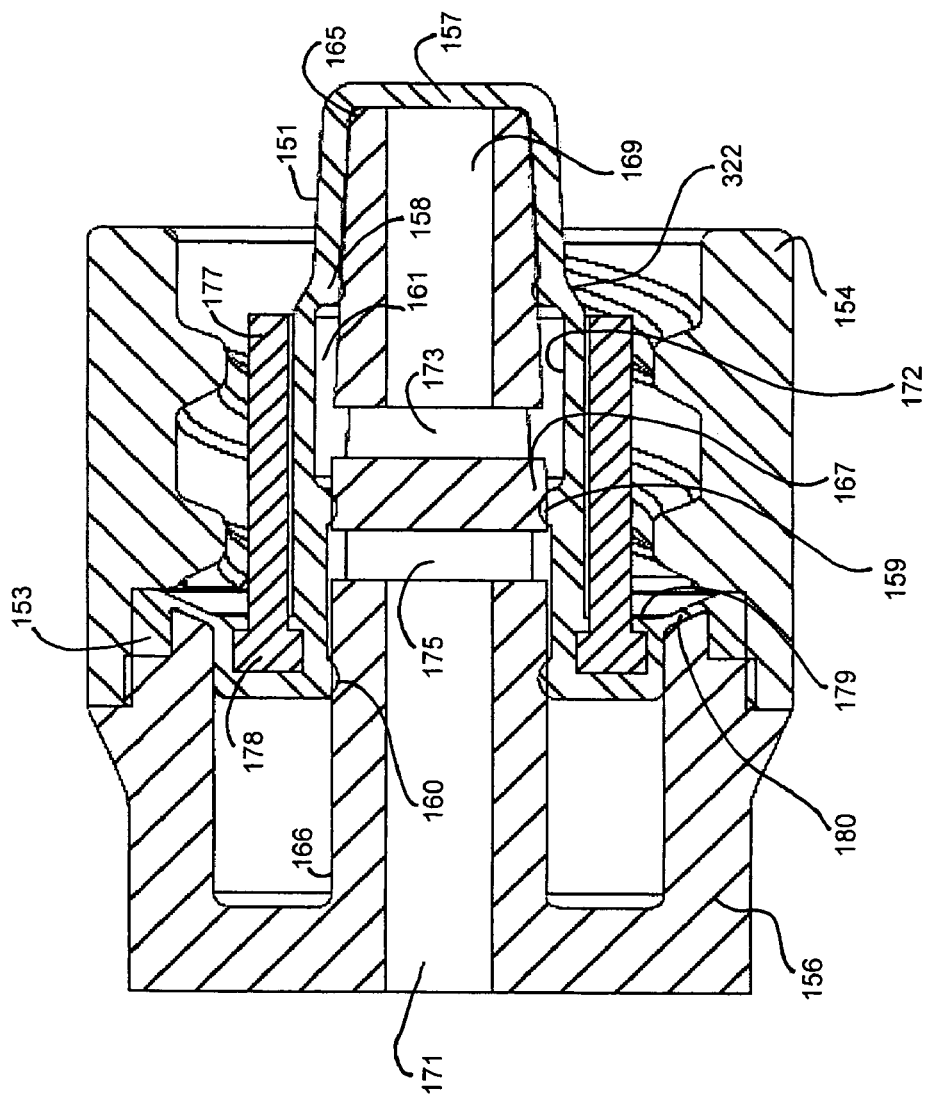
FIG. 23 is a side cut-away view showing an alternative valved fluid connector embodiment.
Figure 24:
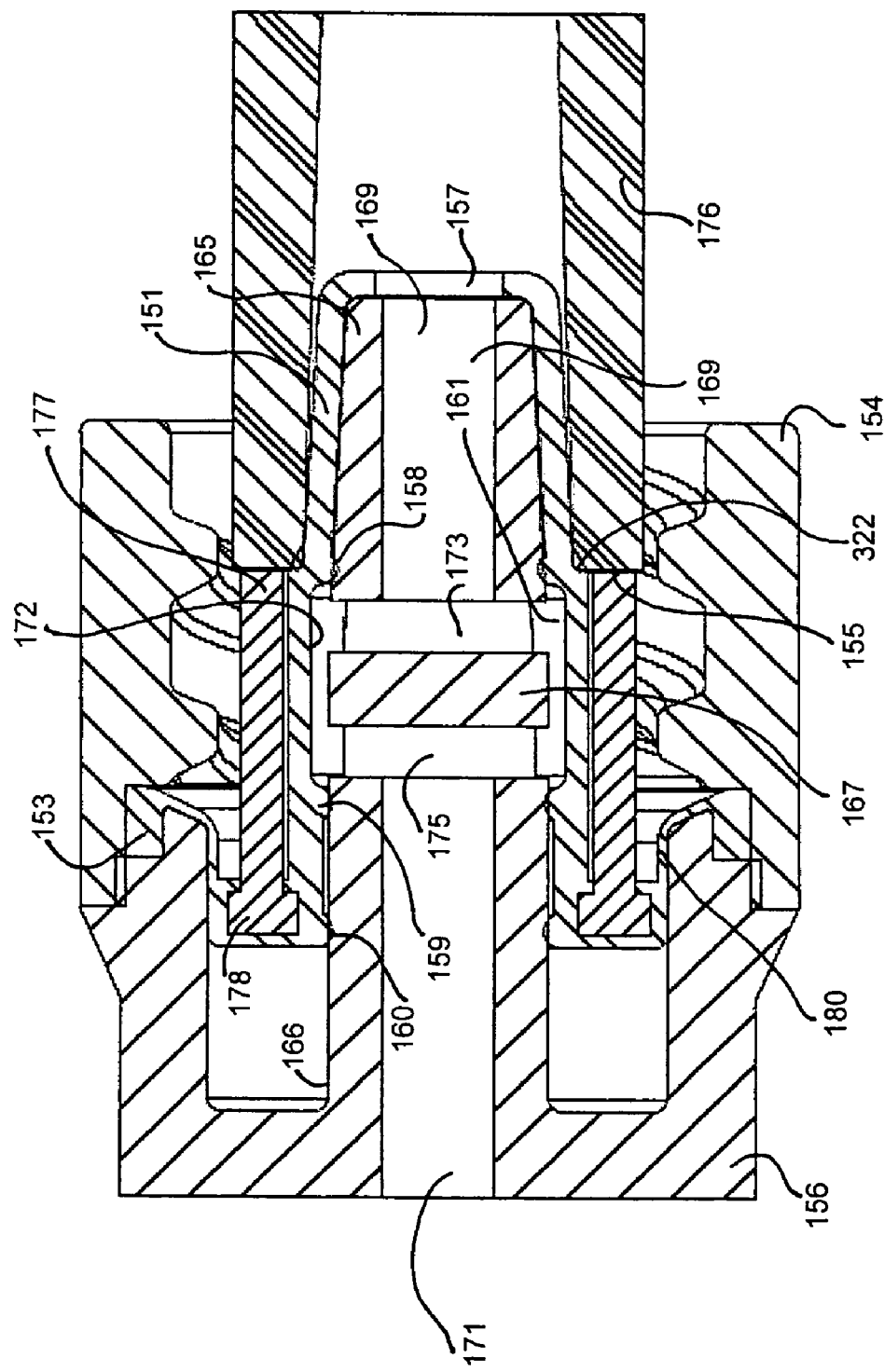
FIG. 24 is a side cut-away view similar to FIG. 23 showing an alternative valved fluid connector embodiment and female connector engaged.

FIGS. 21-25 illustrate another embodiment of a valved male connector comprising a tubular housing, a tubular member comprising opposed flow conduits, an elastic member, and a movable annular collar. Valved male connector comprises an elastic member 151 having a flange section 153 securable by upper housing component 154 and lower housing component 156 suspending membrane section 180 of the flange 153, the elastic member having at its forward end valve member 157. The elastic member 151 has stepped area 322 which provides for at least a portion of the elastic member having an internal diameter greater than the external diameter of the tubular member. As illustrated in FIGS. 23-24, the elastic member 151 further contains a plurality of laterally positioned sliding seals (158, 159, 160) positioned on the inner surface 172 of elastic member 151. Sliding seal 158 is positioned approximately adjacent stepped area 322, sliding seal 159 is positioned rearwardly of sliding seal 158. Movable conduit 161, defined by the larger diameter inner surface 172 of elastic member 151, seal 159, and the outer surface of tubular member 163, provides means for control of the fluid communication between the opposed conduits. The tubular member 163 comprises a distal end 166 and proximal end 165, the proximal end 165 being positioned within the elastic member 151 and in sealable engagement with the valve member 157. The tubular member further comprises an internal wall element 167 between the distal end 166 and proximal ends 165 that forms opposed upper and lower flow conduits, (173 and 175, respectively) substantially perpendicular to an upper and lower axial flow conduits (169 and 171 respectively). The annular collar 177 with lip 178 is positioned between the housing components and the elastic member 151, abutting elastic member 151, movable conduit 161 and in contact with the membrane section 180 of flange section 153, the collar secured to flange section 153 by lip 178.

As illustrated in FIG. 24, during engagement with a female connector the annular collar 177 is urged rearward by a surface 155 of the female connector 176, stretching the membrane section 180 and elastic member 151 and urging the movable conduit 161 over at least a portion of the lower opposed flow conduit 175, the wall element 167 and at least a portion of upper opposed flow conduit 173. In this configuration, fluid communication between the opposed and axial conduits is provided as well as through the tubular member while valve member 157 concurrently opens. Upon disengagement with the female connector 176 the annular collar 177 and conduit 161 are urged forward by the relaxing membrane section 180 and elastic member, positioning seal 159 adjacent wall element 167 ending fluid communication between the opposed and axial conduits and through the tubular member 163, and concurrently closing valve member 157. Stepped area 322 of elastic member provides sealing means during engagement with female connector.

Figure 25:
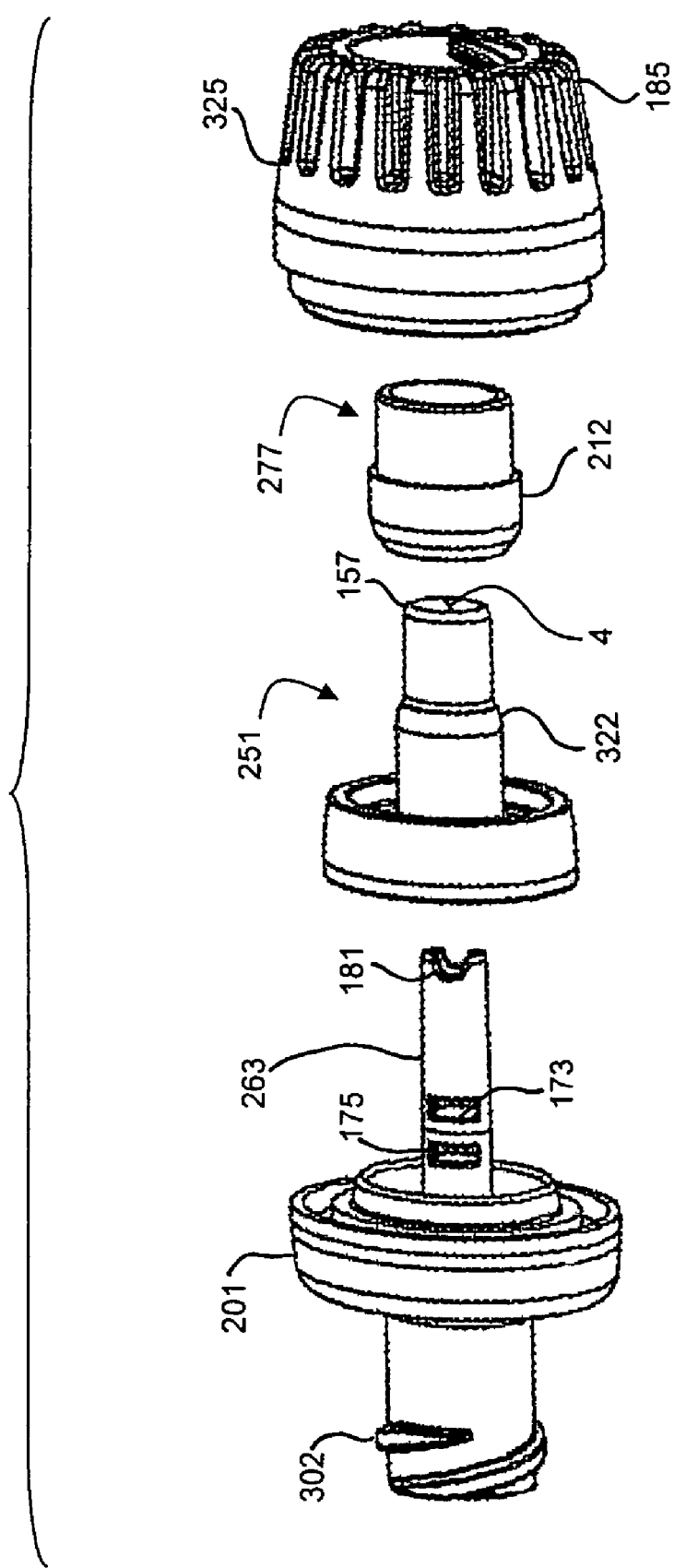
FIG. 25 is an exploded view showing an alternative valved fluid connector embodiment.
Figure 27:
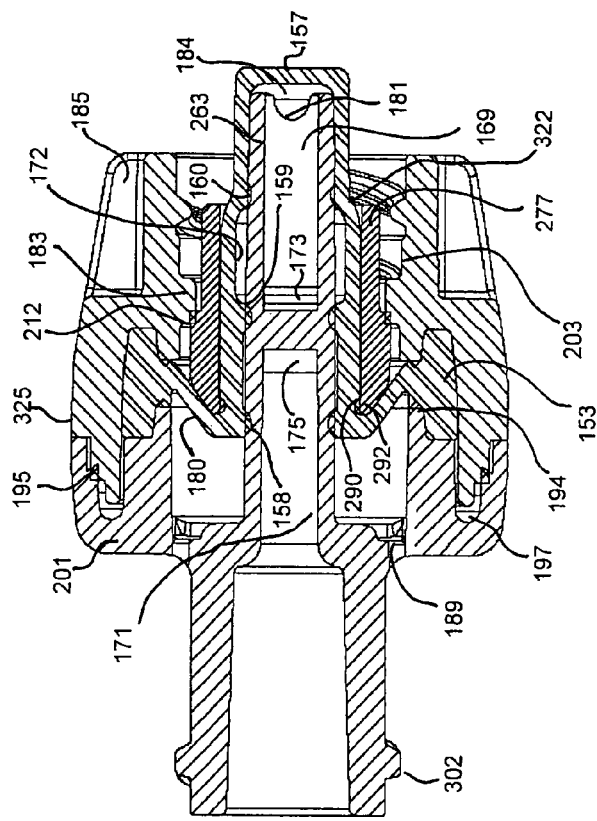
FIG. 27 is a side cut-away view similar to FIG. 26, rotated 90 degrees along the axis of the connector.
Figure 26:
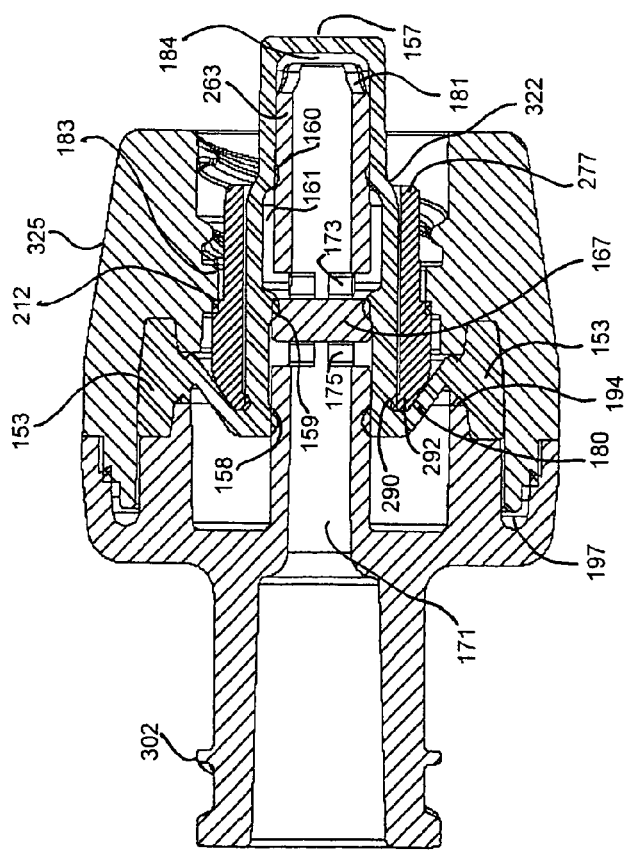
FIG. 26 is a side cut-away view showing an alternative valved fluid connector embodiment.

Alternative embodiments of those illustrated throughout FIGS. 21-24 are depicted in FIGS. 25, 26 and 27. Thus, proximal end of tubular member 263 is chamfered to assist elastic member 251 in stretching around the proximal end of the tubular member and opening valve member 157. Gap 184 between valve member 157 and tubular member proximal end assists to open valve member 157 as elastic member 151 is contacted by female connector surface. Attachment to a standard male luer connector by threaded elements 302 provide universal valved male connector functionality to standard male luer devices by using the embodiments herein described. Annular collar 277 has inwardly extending annular protrusion 290 and angled distal end 292 which contacts with flange for assisting stretching of membrane 180 without tearing or puncturing.

In FIGS. 26 and 27, two views, one rotated 90 degrees along the axis of the connector, of the embodiment of FIG. 25 indicate the following additional or optional elements. Notches 181 provides for better flow with some female needle-free valves by allowing fluid to pass by the opposing face of the internal needle-free valve component during engagement therewith. Cored out ergonomic gripping ribs 185 on the outside surface of the upper housing component 325 assist user in manipulating the device. Stepped in diameter inner housing component 203 provides for a tighter connection via interference with the threads of the female connector and the valved male connector. Vent chambers 189 positioned under elastic member provide for air displacement during engagement.

Also in FIGS. 26 and 27, additional or optional elements of the previous embodiment are shown. Annular collar 277 has laterally extending circumferential lip 212 which abuts interference element 183 causing pre-load of membrane 180 upon assembly. Interference element 183 also provides for limiting the depth of insertion of the female connector and to secure annular collar 177. Energy directors 194 in contact with flange 153 provide for assistance with sealing and retainment of flange 153. Weld interfaces 195 and flash traps 197 provide for ultrasonic welding assembly of upper and lower housing components (325 and 201, respectively).

Figure 29:
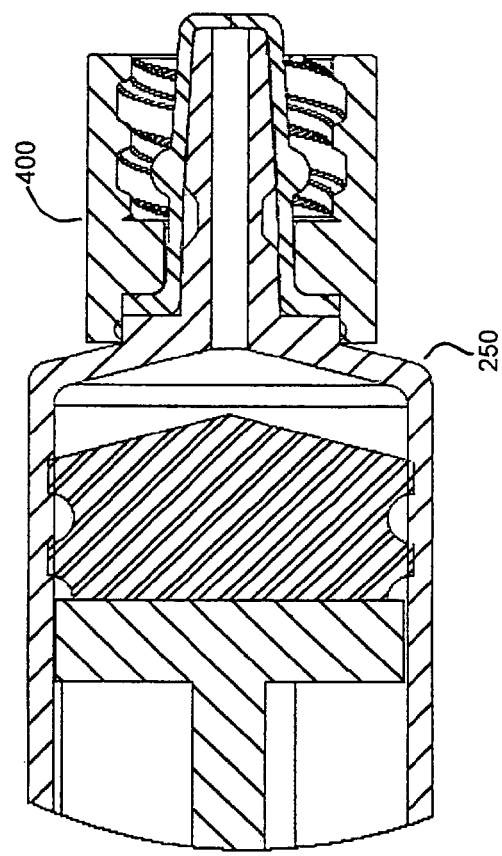
FIG. 29 is a side view showing a valved fluid connector embodiment with a syringe.
Figure 28:
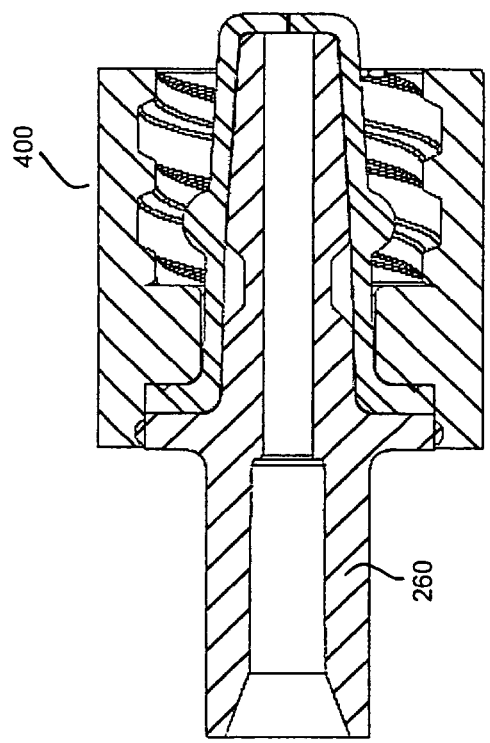
FIG. 28 is a side cut-away view showing a valved fluid connector embodiment for an IV tubing line.
Figure 30:
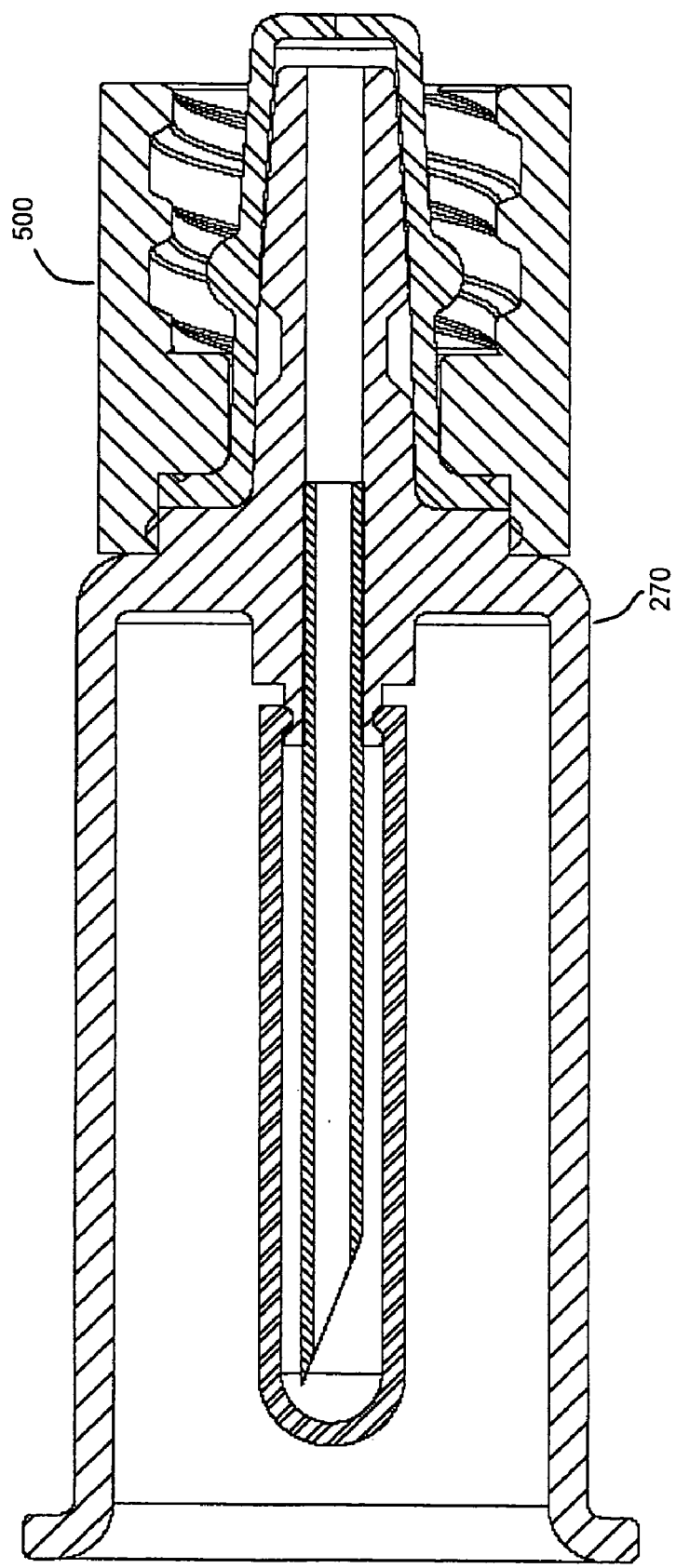
FIG. 30 is a side view showing a valved fluid connector embodiment with a blood collection adapter.

The simplicity and platform nature of the herein disclosed embodiments allows integration with a multiplicity of devices. Referring to FIGS. 28-30, valved fluid connector 400 is adaptable to standard male connectors with tubing pockets 260 or IV tubing sets (FIG. 28), as well as syringe tips 250 (FIG. 29). In addition, valved fluid connector 500 is adaptable to blood collection tube adapters 270 (FIG. 30), etc as well as female luers as previously disclosed. Each of these aforementioned medical devices often containing fluid potentially harmful to patients and/or clinicians which may be reduced or eliminated using the various embodiments herein disclosed. The embodiments herein are generally adaptable to standard male luer connectors to provide valved male luer functionality.

The valve member herein disclosed is preferably not configured in a compressed state or advanced forward from a compressed configuration from within the tubular member to seal the end of the tubular member. The valve member is not preferably configured within or internal to the tubular member. These preferred embodiments may reduce or eliminate the rapid expulsion of fluid droplets or mist out of the valve on disengagement. Thus, the disclosed embodiments offer improved efficacy and safety during use.

The top inside diameter of the valved male tubular member may be similar in size to that of a typical male luer, which typically ranges between 0.050" and 0.120". In one or more embodiment, the inside diameter of the valved male tubular member as the same as most other male luers to be compatible with most any female luer and needle-free valve—including but not limited to those with internal posts. However, the outside diameter of the tubular member may be sufficiently smaller than a typical male luer (as defined by ISO-594-1) to allow room for the elastic member to surround the tubular member and still have clearance between the exterior surface of the elastic member and the female connector inside diameter—at least for the first portion of insertion—to allow the elastic member room to stretch.

The connector housing components will preferably be molded from a thermoplastic resin. The housing components may be designed for assembly using any of the known methods, including but not limited to, ultrasonic welding, bonding, adhesives, solvents, snap-fitting, and the like.

The housing may comprise a plurality of retaining components, for example, to anchor and seal the base of the elastic member, and to keep the entire valved male connector assembly together. The retaining components may further secure the elastic member into position and minimize, reduce or eliminate fluid leakage from its base.

By including an upper retaining ring as a replacement to threaded elements, the valved male connector becomes a "slip luer type". The upper retaining ring may be ultrasonically welded, snapped onto, bonded onto, or similarly affixed to the base of the tubular member, sandwiching the base of the elastic member in-between. By sandwiching the base of the elastic member to the base of the tubular member a seal is created and the elastic member is anchored securely in place. Alternately, the retaining ring can create an interference stop, retaining the elastic member in the embodiments where the elastic member is not attached to the distal base of the tubular member. The retaining ring components are preferably molded from a thermoplastic resin.

In the alternative to the above, by including a retaining threaded hub, the valved male connector becomes of a "luer-locking type". The retaining threaded hub may be ultrasonically welded, snapped onto, bonded onto, or similarly affixed to the base of the tubular member, sandwiching the base of the elastic member in-between. By sandwiching the base of the elastic member to the base of the tubular member a seal is created and the elastic member is anchored securely in place. Alternately, the retaining ring can create an interference stop, retaining the elastic member where the elastic member is not attached to the distal base of the tubular member The threaded hub may be molded from a thermoplastic resin.

The tubular member of the valved male connector may be a rigid or semi-rigid component which defines a fluid passageway. The terms rigid and semi-rigid include the characterization of these terms provided in ISO 594-1 standard. The tubular member also provides the rigid support for the elastic member and surfaces to affix the elastic member or housing components. The tubular member will preferably be molded from a thermoplastic resin. Certain needle free female valves may restrict the flow rate through the valved male connector by blocking fluid flow out the tip of the tubular member. Notches may be provided at the proximal end of the tubular member to create flow paths for fluid to exit the cannula despite a flat surface inhibiting, or a soft surface blocking, or a rough surface hindering, the exit of fluid out of the tip.

In one embodiment, and as exemplified by FIGS. 1-7, an annular groove is located approximately midway down the tubular member in combination with lugs laterally extending from the elastic member. When the female connector pushes the lugs of the elastic member down a predetermined distance, which may be defined by the slit opening to an optimum amount, the lugs fall or are urged into the annular groove so that the tip of the tubular member is prevented from protruding through the slit in the elastic member. This keeps the slit opened to a consistent, optimum amount regardless of how hard or deep the male connector is inserted into a female connector or needle-free valve. The annular groove is sized such that the lugs, when forced by the female connector aid in retaining the attachment of the female connector.

In another embodiment (not shown), a slidable annular collar component may be combined with lugs laterally extending from the elastic member, the lugs may also contain grooves or recesses to receive the annular collar to secure and/or guide the collar when urged rearward.

In various embodiments herein described, and as exemplified by FIGS. 21-27, the tubular member may be designed to redirect the fluid flow path to withstand high pressures at a state of rest or whilst retaining sealing engagement with the female connector or needleless valve connector. Thus, fluid flow is directed into an opposed opening of tubular member, out of one or more first conduits in the side wall of the tubular member, then back into the tubular member via one or more second conduits, then into the engaged female connector. Both first and second conduits are reversibly brought in and out of fluid communication by the movable conduit of the elastic member during engagement and disengagement, respectively. By routing the fluid in such a way, the connector, with a slidable seal in-between the conduits, allows the connector to be pressurized to a greater degree than may otherwise be possible. This may allow the connector to withstand excessive pressures that otherwise would result in bursting or leaking of the connector, for example, pressure generated from pushing forcefully on a syringe, or pressure generated from an IV pump. The addition of the annular collar in combination with the elastic member improves the pressure resistance of the valve significantly by providing lateral support with a generally rigid or semi-rigid cylindrical structure to the elastic member component. The tubular member in this embodiment may further comprise annular recesses to receive the sliding seals during stretching of the elastic member for example, to provide tactile sensation to the user that substantial engagement has occurred.

In various embodiments herein described, and as exemplified in FIGS. 16-18, the tubular member is shaped such that a stepped shoulder with recessed areas positioned in-between is used as an alternative to an annular groove around the tubular member. This alternative restricts the portions of the elastic member in contact with the shoulders from translating downward, thereby focusing most of the stretching to actuate the valve member. Restricting downward translation of portions of the elastic member into opposing areas between the stepped shoulders may more readily return the elastic member, and the valve member may more rapidly reseal, upon disengagement.

The elastic member may be comprised of a silicone or polyurethane material, for example, or any material that possesses inherent resiliency, good sealing properties, radiotransparency, ability to slit, and low compression set properties. Examples of such materials include, but are not limited to, natural rubbers and latex, or synthetic materials such as synthetic polyisoprene, thermoplastic elastomer, thermoset rubber, latex-free rubber, etc.

The elastic member may be formed by way of compression molding, transfer molding, injection molding, reactive injection molding (RIM), liquid injection molding (LIM) or other similar means. The elastic member component may be molded, and then slit either just prior to ejection from the tool, or as a secondary operation. A slitting blade or other piercing member may be used to form the slit. The slit length dimensions may range between 0.050" up to the full distance across the tip of the male luer and may include a distance that extends to and along the sides of the elastic member, such distances typically may be about 0.160". The slit length is generally determined such that it opens sufficiently to provide adequate flow through the connector; however, the tubular member component need not, but may, protrude through the slit opening for flow. Alternatively, the slit may traverse across the whole tip, allowing the male connector rigid component to protrude from within. The shape of the slit may be a single slit, cross slit or other suitable shape. The slit in the valve member may be formed during the fabrication of the elastic member or in a post-fabrication process. Lubricants may be added to the elastic member material or onto the material to facilitate low-friction activation and return. Such lubricants include those approved for medical use, for example, medical grade silicone fluids.

Depth-limiting means, as exemplified in FIGS. 5-18, may be used to limit the actuated depth of the elastic member so as to prevent the tip of the tubular member from protruding through the slit in the elastic member. This may be done with inwardly projecting annular groove in the tubular member, or inwardly projecting shoulder protrusion in the rigid housing components. Depth limitation provides consistent slit opening dimensions, resealing consistency during each use, maximization of flow, and prevention of inadvertent damage.

The elastic member functions to open and close the valve member as well as to seal the tubular member passageway to eliminate leakage under normal pressure conditions. The elastic member is activated by stretching. For example, in various embodiments, the return force of the elastic member may be generated by the elongational tension or stretching within the elastic member between the lugs and slit. Upon removal of the female connector or needle-free valve from the valved male connector, this elongational tension stored in the component will provide the energy required to return the elastic member to the unstretched position, thus allowing the slit to re-close and any sliding seals to return to the unstretched, sealed closed position.

In other embodiments, the return force of the elastic member is substantially generated by the stretching of the elastic member, either from the translating lugs/annular collar and slit, or from the stretching membrane and flange, as shown for example in FIGS. 19-27. Upon removal of a female connector or needle-free valve from the valved male connector, this tension stored in the elastic member provides energy to return the elastic member to the before-tensioned position, thus allowing the slit to re-close and any sliding seals to return to the before-tensioned, sealed closed position.

Upon initial insertion with a female connector or needle-free valve, the forward end of the elastic member may function as a clearance fit, until coming into contact with the external lugs or annular collar. This clearance fit may facilitate the opening process of the slit and will act as a normal male connector tip, which is also designed to be a clearance fit with standard female connectors and needle-free valves for the first portion of insertion. In one or more embodiments, the elastic member has a 6% or similar luer-like taper such that during and after complete engagement, the elastic member will interfere with the female connector to create a seal.

The elastic member and valve member are designed for compatibility with various needle-free valves including needle-free valves having posts. The post of such valves will pass through the slit opening and into the tubular member allowing for unrestricted flow.

As the opening in the elastic member and the inside of the tubular member have generally the same dimensions as a standard male connector tip, this invention will allow for adequate flow with needle-free valves and standard female luers that are designed to accessed by a standard male connector tip.

For example, in FIG. 5, the slit may be first biased open by axial pressure to the valve member by the swab-able top of a needle-free valve. Then upon full insertion, the slit is further stretched open to the full, optimal amount by translation of the laterally extended lugs or annular collar.

Both the inside of the tip of the elastic member and outside edge of the tubular member tip may be chamfered. This mating chamfer will act to direct the slit open, out and down, when acted upon by the swab-able surface of a needle-free valve. Further, when the lugs or annular collar are urged rearward, this mating chamfer will ease the opening of the slit during its activation. Alternately, these chamfers may be generous radii.

In FIGS. 25, 26 and 27, cutouts or grooves in the tip of the tubular member cannula allow improved compatibility and fluid flow with female connector valves that have internal valve mechanisms. Alternatively, (not shown) the tip of the elastic member may contain a "duckbill-type" valve to increase pressure resistance at the tip. The angled surfaces of the duckbill valve may mate with similar surfaces at the inside diameter of the tubular member tip, assisting the opening of the valve member as they slide upon each other.

Annular sliding seals within the inside diameter of the elastic member are disclosed, for example, in FIGS. 22-24, and 26-27. These seals slidably engage with the external surface of the tubular member. In FIGS. 22-24, and 26-27, three seals are shown. In a preferred embodiment, three sliding seals are used to achieve increased pressure resistance (the primary seal being between the top and bottom axial conduits of the tubular member side wall) when disengaged. When disengaged, the sliding seals isolate the bottom axial conduit from the top axial conduit and tip of the tubular member, thus withstanding back-pressures that may be generated from various sources—such as syringe pressures, IV pump pressures, etc. The lowest most seal holds back fluid preventing it from entering into the space below the elastic member flange. The middle seal is the primary seal blocking fluid flow between the opposed conduits and preventing fluid flow through the tubular member. When the valve is engaged or actuated, the middle seal moves below the opening of the bottom opposed conduit, allowing fluid communication between the bottom and the upper axial conduits, or vice versa. The upper seal (closest to the male connector tip), confines the fluid to a space and thus defines a movable flow path (laterally extending movable conduit) between the upper and middle seals, allowing flow between the axial conduits and through the tubular member.

In various embodiments herein described, the elastic member is placed into a tensioned-elongated or stretched configuration. Although not to be held to any theory or belief, it is believed that stretching tension is more repeatable and predictable in ensuring that the resealable valve member will return to its closed configuration each time the connector is actuated or engaged. In contrast, a compressive configuration normally results in buckling, compression set and an unacceptable range of actuation forces and/or low return forces. Thus, by applying stretching forces to the elastic member consistent and repeated forces will be generated during activation, in contrast to buckling or compressive loading forces which may act differently each time.

The elastic member is stretched when actuated due to the forces transferred from the female connector, or by way of the annular collar. A stretchable membrane and/or flange, which may be anchored between housing retaining components and/or the base of the tubular member, may be used as depicted in FIGS. 19-27. When actuated, the membrane stretches, and when deactivated, the membrane elastically returns.

In various embodiments herein described and exemplified in FIGS. 1-18, the valved fluid connector comprises laterally extending lugs integral with the elastic member. These lugs, located approximately mid-way down or lower normally interface with the leading edge and face of a female connector. When forced rearward by the female connector, the lugs stretch at least a portion of the elastic member between the reversibly sealable slit and the lugs, thereby opening the slit. The lugs may be an annular ring around the elastic member, or a plurality of laterally protruding features. These lugs are generally compatible with most if not all female connectors and needle-free valve designs as they will not normally interfere with their operation. The lugs may also assist in retaining the female component onto the valved male connector via an interference fit during engagement.

The lugs laterally extending from the elastic member are located at an approximately 180 degrees apart as viewed from a top view; alternatively, they would extend radially outward from the circumference of the tubular member. The lugs may be positioned perpendicular to the slit in order to maximize slit opening.

In various embodiments, an annular collar is used, for example in FIGS. 19-27. With the inclusion of the annular collar, the pressure resistance imparted by the sliding seals may be increased. By backing up, or providing support to the seals, blow by from internal pressure on the seals may be eliminated or reduced as the annular collar keeps the seals physically engaged with the outside diameter of the tubular member. The collar also allows the female connector to engage fully with male connector lock threads while keeping the elastic member stretched or in tension during actuation/engagement. By including an annular collar in various embodiments, the tensile loads may be efficiently applied and/or distributed to the elastic member, for example, to the integrated stretchable flange, keeping the entire elastic member in tension. Additionally, friction between the female connector or needle-free valve and the annular collar may be lower than if the female connector were engaged against an elastomer, thereby reducing overall friction in the system and easing actuation by the user. The annular collar may be molded from a thermoplastic resin or may be constructed by insert molding the collar as part of the elastic member. This latter option reduces one additional assembly step, and keeps the annular collar securely in position. Alternately, the annular collar may be snapped into place into an undercut in the elastic member component. The annular collar may comprise a reverse taper or stepped bottom portion that may be snapped into a corresponding circumferential recess or undercut in the flange, keeping the collar-flange assembly adequately positioned during use or in assembly. Alternately, the annular collar may be bonded into place using an adhesive (UV, cyanoacrylate, etc.) to a circumferential recess or undercut in the elastic member. Optionally, overlapping shelves may be added on both the annular collar and a locking retaining component to keep the annular collar from being removed or dislodged once the parts are assembled.

For simplicity in a number of the figures the female connector is not itself shown and only the movement of elements of the male connector is illustrated. It will be understood that such movement is the result of the male/female connector engagement in the manner illustrated in other figures. Similarly, threads or other securing devices to retain the male and female connectors during use, or standard male luer adaptors on the housing are also, for simplicity, not shown in all figures, but it will understood that such are present.

Although some exemplary embodiments of the invention have been described above by way of example only, it will be understood by those skilled in the field that modifications may be made to the disclosed embodiments without departing from the scope of the invention, which is defined by the appended claims.

The invention claimed is:

1. A valved male connector for providing fluid flow comprising:
   a tubular housing having an outer surface and an inner surface, a proximal end and a distal end, the proximal end engagable with a female connector;
   a tubular member positioned within the housing comprising:
      an axial conduit between a proximal end and a distal end;
      an outer surface; and
      an internal wall element forming an upper and lower opposing conduit, the
      wall element bisecting the axial conduit into an upper and lower axial conduit;
   an elastic member comprising:
      a forward and a rearward end, the forward end adjacent the proximal end of the tubular housing;
      a flange section positioned at the reward end securable within the tubular housing;
      a first laterally protruding sliding seal on the interior surface of the elastic member adjacent the exterior surface of the tubular member;
      an interior surface portion having a diameter larger than the diameter of the tubular member exterior surface positioned forwardly from the first laterally protruding sliding seal;
      a valve member integral with the forward end and in sealing relationship with the proximal end of the tubular member; and
      a movable conduit defined by the first laterally protruding sliding seal, the
   interior surface portion and outer surface of the tubular member; and an annular collar located within the housing between the elastic member and the tubular housing and in contact with the flange section, the annular collar slidably movable between the tubular housing and the elastic member.

2. The valved male connector of claim 1, wherein the movable conduit is spaced to include the internal wall element and at least a portion of the upper opposed conduit and at least a portion of the lower opposed conduit.

3. The valved male connector of claim 1, wherein prior to engagement with a female connector the first laterally protruding sliding seal of the elastic member is positioned as to prohibit fluid communication between the lower and upper axial conduits.

4. The valved male connector of claim 3, wherein prior to engagement with a female connector the first laterally protruding sliding seal is positioned adjacent to at least a portion of the internal wall element of the tubular member.

5. The valved male connector of claim 1, wherein during disengagement with a female connector the movable conduit of the elastic member is positioned as to allow fluid communication between the lower and upper axial conduits.

6. The valved male connector of claim 5, wherein during engagement with a female connector the first laterally protruding sliding seal is positioned rearwardly of at least a portion of the lower opposed conduit of the tubular member.

7. The valved male connector of claim 1, wherein during disengagement with a female connector the first laterally protruding sliding seal of the elastic member is positioned as to prohibit fluid communication between the lower and upper axial conduits by unstretching of the elastic member.

8. The valved male connector of claim 1, wherein engagement with a female connector urges the annular collar and movable conduit of the elastic member rearwardly from the proximal end of the tubular member elongating at least a portion of the elastic member and opening the valve member.

9. The valved male connector of claim 8, wherein engagement with a female connector further provides slidably positioning the movable conduit to include at least a portion of the lower opposed conduit, at least a portion of upper opposed conduit and the internal wall element permitting fluid communication from the proximal end of the tubular portion to the female connector.

10. The valved male connector as claimed in claim 1, wherein engagement with a female connector urges the annual collar rearwardly from the proximal end of the tubular member elongating at least a portion of the elastic member, opening the valve member, positioning the first laterally protruding sliding seal rearwardly of the lower opposed conduit and permitting fluid communication between the opposed conduits and axial conduits of the tubular member 11. The valved male connector of claim 1, further comprising a second laterally protruding sliding seal on the interior of the elastic member positioned rearwardly of the first laterally protruding sliding seal.

12. The valved male connector of claim 1, further comprising a third laterally protruding sliding seal on the interior of the elastic member positioned forwardly of the first laterally protruding sliding seal and forwardly of the internal wall element.

13. The valved male connector of claim 1, wherein the elastic member further comprises a laterally extending protrusion.

14. The valved male connector of claim 13, wherein the annular collar, upon engagement with a female connector surface, axially displaces the laterally extending projection causing stretching of the elastic member.

15. The valved male connector of claim 1, wherein the elastic member further comprises an interference element for securing the annular collar.

16. The valved male connector of claim 1, wherein the valve member comprises a slit.

17. The valved male connector of claim 16, wherein the slit comprises a cross-slit.

18. The valved fluid connector as claimed in claim 16, wherein engagement with the female connector opens the slit and upon disengagement with the female connector closes the slit.

19. The valved male connector of claim 1, wherein the valve member comprises a duck-bill valve.

20. The valved male connector as claimed in claim 1, wherein the elastic member is a silicone elastomer material.

21. The valved male connector as claimed in claim 1, wherein the elastic member is selected from the group consisting of polyurethane elastomers, thermoplastic elastomers, and thermoset rubbers.

22. The valved male connector of claim 1, wherein the annular collar comprises a rigid or semi-rigid material.

23. The valved male connector of claim 1, wherein the annular collar is secured to the elastic member.

24. The valved male connector of claim 23, wherein the annular collar is integral with the elastic member.

25. The valved male connector of claim 1, wherein the tubular housing further comprises a lower housing component lockable to an upper housing component.

26. The valved male connector of claim 1, wherein the flange of the elastic member is secured between the lower housing component and the upper housing component forming a membrane.

27. The valved male connector of claim 1, wherein the tubular housing comprises securing means adjacent the forward end for releaseable engagement with the female connector for releaseably securing the connectors together.

28. The valved male connector of claim 1, wherein the tubular housing comprises depth-limiting means to limit the depth of a female connector during engagement.

29. The valved male connector of claim 1, wherein the housing comprises interference means to secure the annular collar within the housing.

30. The valved male connector of claim 29, wherein the interference means pretensions the elastic member without engagement of a female connector.

31. The valved male connector of claim 1, wherein the tubular member is comprised of rigid or semi-rigid material.

32. The valved male connector of claim 1, wherein the tubular member comprises depth-limiting means.

33. The valved male connector of claim 1, further comprising the tubular member extending co-axially beyond the forward end of the housing.

34. The valved male connector of claim 1, wherein the tubular member comprises at least one notch at the proximal end.

35. A valved male connector assembly comprising:
- a tubular section having an axial conduit between a proximal end and a distal end, an outer surface and an internal wall element forming an upper and lower opposing conduit bisecting the axial conduit into an upper and lower axial conduit;
- an elastic member comprising: a forward and a rearward end;
- a flange section positioned at the reward end; a first laterally protruding sliding seal on the interior surface of the elastic member adjacent the exterior surface of the tubular member;
- an interior surface portion having a diameter larger than the diameter of the tubular member exterior surface positioned forwardly from the first laterally protruding sliding seal;

a valve member integral with the forward end and in sealing relationship with the proximal end of the tubular member; and a movable conduit defined by the first laterally protruding sliding seal, the interior surface portion and outer surface of the tubular member;

an annular collar abutting the elastic member, the annular collar slidably movable with the elastic member;

wherein contact with a female connector positions the movable conduit to include at least a portion of the lower opposed conduit, the internal wall and at least a portion of the upper axial conduit permitting fluid communication between the lower and upper axial conduits.

36. A valved male connector for providing fluid flow comprising:

a tubular housing having a proximal end and a distal end and an inner and outer wall, the proximal end engagable with a female connector;

a tubular member positioned within the housing and having a proximal end and a distal end;

an elastic member with a forward end and a rearward flange end, the forward end surrounding the tubular member, a valve member at the forward end of the elastic member and in sealing relationship with the proximal end of the tubular portion, the valve member being biased by the elastic member; and an annular collar located within the housing between the elastic member and the inner wall of the housing and in contact with the flange, the annular collar slidably movable between the tubular housing and the elastic member, wherein the annular collar upon engagement with a female connector surface causes stretching of the elastic member, biasing the valve member.

37. The valved male connector of claim 36, wherein the elastic member further comprising a laterally extending protrusion.

38. The valved male connector of claim 36, wherein the annular collar, axially displaces the laterally extending projections causing stretching of the elastic member.

39. The valved male connector of claim 36, wherein the valve member comprises a slit.

40. The valved male connector of claim 39, wherein the slit comprises a cross-slit.

41. The valved male connector of claim 36, wherein the valve member comprises a duck-bill valve.

42. The valved male connector of claim 36, wherein engagement with the female connector deforms the slit to open the valve and upon disengagement with the female connector deformation of the slit is reversed to close.

43. The valved male connector of claim 36, wherein the tubular member comprises at least one notch.

44. The valved male connector of claim 36, wherein the elastic member is a silicone elastomer material.

45. The valved male connector of claim 36, wherein the elastic member is selected from the group consisting of polyurethane elastomers, thermoplastic elastomers, and thermoset rubbers.

46. The valved male connector of claim 36, wherein the annular collar comprises a rigid or semi-rigid material.

47. The valved male connector of claim 36, wherein the annular collar is secured to the elastic member.

48. The valved male connector of claim 36, wherein the annular collar is integral with the elastic member.

49. The valved male connector of claim 36, wherein engagement with a female connector urges the annular collar rearwardly from the proximal end of the tubular member elongating at least a portion of the elastic member, opening the valve member and permitting fluid communication between the proximal end of the inner tubular portion and a female connector.

50. The valved male connector of claim 36, wherein the tubular housing further comprises a lower housing component lockable to an upper housing component.

51. The valved male connector of claim 50, wherein the elastic member flange is secured between the upper housing components and lower housing components of the tubular housing.

52. The valved male connector of claim 36, wherein the tubular housing further comprises securing means adjacent the forward end for releaseable engagement with the female connector for releaseably securing the connectors together.

53. The valved male connector of claim 36, wherein the tubular housing further comprises depth-limiting means to limit the depth of a female connector during engagement.

54. The valved male connector of claim 36, wherein the tubular housing further comprises interference means to secure the annular collar within the housing.

55. The valved male connector of claim 54, wherein the interference means pretensions the elastic member without engagement of a female connector.

56. The valved male connector of claim 36, wherein the tubular member is comprised of rigid or semi-rigid molded material.

57. The valved male connector of claim 36, wherein the tubular member comprises depth-limiting means adjacent the distal end.

58. The valved male connector of claim 36, further comprising the tubular member extending co-axially beyond the forward end of the housing.

59. A fluid connector comprising:

a housing;

an elastic member comprising a forward end integral with a valve member and a rearward end comprising a flange secured within the housing;

a tubular member with a proximal end positioned within the elastic member;

the proximal end of the tubular member in sealing relationship with the valve member of the elastic member and a distal end secured to the housing;

an annular collar member located between the housing and the elastic member and in contact with the flange, the annular collar member slidably movable between the housing and the elastic member; wherein the annular collar member is urged rearwardly from the tubular member proximal end stretching the elastic member and opening the valve member wherein engagement with a female connector urges the annular collar rearwardly from the proximal end of the tubular member elongating at least a portion of the elastic member, opening the valve member and permitting fluid communication with the female connector.

60. A valved male connector comprising:

a housing;

a tubular member contained within the housing with a proximal end and a distal end, a first stepped area and a second stepped area positioned forwardly of the first stepped area defining a first groove;

an elastic member comprising:

forward and rearward ends; an interior and exterior surface, the interior surface adjacent the tubular member;

at least one lateral protrusion on the exterior surface;

and a valve member at the forward end of the elastic member and in reversible sealing relationship with the proximal end of the tubular member wherein a female connector surface axially displaces the lateral projection causing stretching of the elastic member.

61. The valved male connector of claim 60, wherein insertion into a female connector urges the protrusion rewardly effecting the elastic member into a stretched configuration and opening the valve member permitting fluid communication from one connector to another.

62. The valved male connector of claim 60, wherein insertion into a female connector urges the protrusion into the first groove effecting the elastic member into a stretched configuration and opening the valve member permitting fluid communication from one connector to another.

63. The valved male connector of claim 60, wherein disengagement of the connectors provides for unstretching of the elastic member closing the valve member and preventing fluid flow through the valved male connector.

64. The valved male connector of claim 60, wherein the rearward end of the elastic member and the distal end of the tubular member are secured to each other.

65. The valved male connector of claim 60, wherein the rearward end of the elastic member and the distal end of the tubular member are unattached.

66. The valved male connector of claim 60, wherein the tubular member is comprised of rigid or semi-rigid material.

67. The valved male connector of claim 60, wherein valve member is integral with the elastic member.

68. The valved male connector of claim 60, wherein the elastic member further comprises an annular inwardly projecting lateral protrusion adjacent the inner surface of the rearward end in sealing engagement with the groove of the tubular member.

69. The valved male connector of claim 60, wherein the elastic member and the valve member are made of silicone elastomer material.

70. The valved male connector of claim 60, wherein the elastic member and the valve member are selected from the group comprising polyurethane elastomers, thermoplastic elastomers, and thermoset rubbers.

71. The valved male connector of claim 60, wherein the valve member comprises a slit at an end thereof, and upon engagement with the female connector the slit opens and upon disengagement with the female connector the slit closes.

72. The valved male connector of claim 71, wherein the slit is approximately perpendicular to the laterally extending protrusions.

73. The valved male connector of claim 60, wherein the valve is a duck-bill valve.

74. The valved male connector of claim 60, wherein the housing comprises securing means adjacent the forward end for releaseable engagement with the female connector for releaseably securing the connectors together.

75. The valved male connector of claim 60, wherein the housing comprises depth-limiting means.

76. A valved male connector of claim 60, wherein the tubular member comprises depth-limiting means.

77. The valved male connector of claim 60, wherein the tubular member extends co-axially beyond the forward end of the housing.

78. The valved male connector of claim 60, wherein the tubular member comprises a notch at the proximal end.

79. A valved male assembly comprising:
a tubular portion comprising:
a proximal end; and
a first stepped area and a second stepped area positioned forwardly from the first stepped area forming a groove;
an elastic member comprising: a forward end surrounding the proximal end of the tubular portion; and
a rearward end surrounding at least a portion of the groove but not secured to the distal end of the tubular portion;
laterally extending protrusions positioned between the forward and rearward end; and
a valve member at the forward end of the elastic member, the valve member in sealing relationship with the proximal end of the tubular portion;
wherein sealable engagement with a female connector contacts the laterally extending protrusions urging the elastomeric member into a stretched position opening the valve member.

80. A valved male connector comprising:
a tubular member having a proximal end; and
an elastic member surrounding the tubular member proximal end the elastic member having a forward end, the forward end integral with a valve member in sealing relationship with the proximal end of the tubular member, the elastic member upon contact with a female connector further having means for reversibly transitioning between an unstretched configuration and a stretched configuration;
wherein the valve member is in sealing relationship with proximal end of tubular member when the elastic member is in an unstretched configuration and the valve member is in an unsealing relationship with proximal end of tubular member when the elastic member is in a stretched configuration.

81. A valved fluid connector comprising:
a tubular member having a distal end, a proximal end and a stepped area spaced distally from the proximal end;
an elastic member comprising: inner and outer surfaces;
laterally extending protrusions projecting from the outer surface; and
opposite rearward and forward ends, the forward end surrounding the proximal end of the tubular member and the rearward end surrounding a portion of the stepped area of the tubular member, wherein the rearward end of the elastic member and the distal end of the tubular member are unattached; and
a valve member at the forward end of the elastic member, the valve member in sealing relationship with the proximal end of the tubular member
wherein stretching of the elastic member by a female connector contact surface during engagement therewith, opens the valve member to permit fluid communication between both connectors.

82. The valved fluid connector of claim 81, wherein engagement with a female connector urges the laterally extending protrusions rearwardly and stretches the elastic member.

83. The valved fluid connector of claim 81, the elastic member comprising an outwardly protruding lip on the outer surface adjacent the rearward end.

84. The valved fluid connector of claim 81, wherein unstretching of the elastic member upon disengagement of the connectors provides closing of the valve member to prevent fluid flow through the valved fluid connector.

85. The valved fluid connector of claim 81, wherein the tubular member is comprised of rigid or semi-rigid material.

86. The valved fluid connector of claim 81, wherein the elastic member and the valve member are made of silicone elastomer material.

87. The valved fluid connector of claim 81, wherein the elastic member and the valve member are selected from the group consisting of polyurethane elastomers, thermoplastic elastomers, and thermoset rubbers.

88. The valved fluid connector of claim 81, wherein the valve member comprises a slit.

89. The valved fluid connector of claim 88, wherein the laterally extending protrusions are approximately perpendicular to the slit 90. The valved fluid connector of claim 81, wherein the valve comprises a duck-bill valve 91. The valved fluid connector of claim 81, wherein the tubular member comprises a notch at the proximal end.

92. The valved fluid connector of claim 81, further comprising a housing having an outer portion with a rear end and a forward open end, the tubular member being disposed at least partially within and connectable to the housing.

93. The valved fluid connector of claim 92, wherein the housing comprises securing means adjacent the forward end for releaseable engagement with the female connector for releaseably securing the connectors together.

94. The valved fluid connector of claim 92, wherein the housing is generally cylindrical in shape and comprises threads on an internal surface of the outer tubular portion for engaging complementary threads on a female connector.

95. The valved fluid connector of claim 92, wherein the housing comprises depth-limiting means.

96. The valved fluid connector of claim 81, wherein the tubular member extends co-axially beyond the forward end of the housing.

97. A method for improving human safety during manipulation or transfer of fluid or chemical agents comprising:

a) providing contact of a fluid or chemical agent with a valved male connector, the valved male connector comprising:

a housing;

an elastic member comprising a forward end integral with a valve member and a rearward end comprising a flange secured within the housing;

a tubular member with a proximal end positioned within the elastic member;

the proximal end of the tubular member in sealing relationship with the valve member of the elastic member and a distal end secured to the housing; and an annular collar member located between the housing and the elastic member and in contact with the flange, the annular collar member slidably movable between the housing and the elastic member, wherein engagement with a female connector contact surface moves the annual collar causing stretching of the elastic member, opening the valve member to permit fluid communication between both connectors;

and b) transferring or manipulating the fluid or chemical agent.

98. The method of claim 97, wherein the chemical agents are chemotherapy agents.

* * * * *

UNITED STATES PATENT AND TRADEMARK OFFICE
CERTIFICATE OF CORRECTION

PATENT NO. : 7,559,530 B2 Page 1 of 1
APPLICATION NO. : 11/353275
DATED : July 14, 2009
INVENTOR(S) : Todd M. Korogi, Scott P. Jarnagin and Theodore J. Mosler It is certified that error appears in the above-identified patent and that said Letters Patent is hereby corrected as shown below:

Column 17, line 15, please delete "disengagement" and insert in place thereof
-- engagement --

Column 17, line 41, please delete "annual" and insert in place thereof -- annular --

Signed and Sealed this

Eighth Day of September, 2009

David J. Kappos
*Director of the United States Patent and Trademark Office*